United States Patent
Shim et al.

(10) Patent No.: US 10,064,939 B2
(45) Date of Patent: Sep. 4, 2018

(54) COMBINATION THERAPY USING C-MET INHIBITOR AND IGF-1R INHIBITOR FOR C-MET INHIBITOR RESISTANT CANCERS

(71) Applicants: Samsung Electronics Co., Ltd., Suwon-si, Gyeonggi-do (KR); Yonsei University, University-Industry Foundation (UIF), Seoul (KR)

(72) Inventors: Seon Hui Shim, Daejeon (KR); Ji Min Lee, Seoul (KR); Soo Yeon Jung, Seongnam-si (KR); Woo Sun Kwon, Seoul (KR); Kyung Ah Kim, Seongnam-si (KR); Jeong Min Kim, Seoul (KR); Sun Young Rha, Seoul (KR); Won Suk Lee, Seoul (KR)

(73) Assignees: SAMSUNG ELECTRONICS CO., LTD., Suwon-si (KR); YONSEI UNIVERSITY, UNIVERSITY-INDUSTRY FOUNDATION (UIF), Seoul (KR)

( * ) Notice: Subject to any disclaimer, the term of this patent is extended or adjusted under 35 U.S.C. 154(b) by 0 days.

(21) Appl. No.: 14/949,041

(22) Filed: Nov. 23, 2015

(65) Prior Publication Data

US 2016/0144027 A1 May 26, 2016

(30) Foreign Application Priority Data

Nov. 21, 2014 (KR) .................. 10-2014-0163792

(51) Int. Cl.
```
A61K 39/395    (2006.01)
A61K 31/00     (2006.01)
C07K 16/28     (2006.01)
A61K 31/4985   (2006.01)
G01N 33/574    (2006.01)
G01N 33/74     (2006.01)
A61K 39/00     (2006.01)
```

(52) U.S. Cl.
CPC ........ *A61K 39/39558* (2013.01); *A61K 31/00* (2013.01); *A61K 31/4985* (2013.01); *C07K 16/2863* (2013.01); *G01N 33/57492* (2013.01); *G01N 33/74* (2013.01); *A61K 2039/505* (2013.01); *C07K 2317/24* (2013.01); *C07K 2317/52* (2013.01); *C07K 2317/622* (2013.01); *C07K 2317/92* (2013.01); *C07K 2319/00* (2013.01); *G01N 2333/65* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,178,668 B2 * | 5/2012 | Steinig ................ | C07D 401/04 544/128 |
| 8,563,696 B2 | 10/2013 | Cheong et al. | |
| 9,402,918 B2 * | 8/2016 | Koyakutty ........... | A61K 31/437 |
| 2009/0068110 A1 * | 3/2009 | Shang .................. | A61K 31/337 424/9.2 |
| 2011/0129456 A1 * | 6/2011 | Wang ................. | A61K 31/4745 424/131.1 |
| 2014/0057898 A1 | 2/2014 | Stefanic et al. | |

FOREIGN PATENT DOCUMENTS

| | | |
|---|---|---|
| KR | 2006-0008945 A | 1/2006 |
| KR | 2011-0047698 A | 5/2011 |
| WO | WO 2013/152252 A1 | 10/2013 |

OTHER PUBLICATIONS

Ueno et al., Combination of selective ALK inhibitor ASP3026 with inhibition of IGF-1R signaling overcomes crizotinib resistance in NCI-H2228 human NSCLC Cells. Eur. J. of Cancer, 48, No. Suppl. 6, p. 52, 2012.*
Sahu et al., Crizotinib: A comprehensive review. South Asian J. Cancer. 2, 91-97, 2013.*
Rudikoff et al., Single amino acid substitution altering antigen-binding specificity. Proc. Nat. Acad. Sci. USA 79, 1979-1983, 1982.*
Coley, "Methods in Molecular Medicine", *Cancer Cell Culture*, 88: pp. 267-273 (2004) Abstract.
Inou et al. "In vitro evaluation of anticancer drugs in relation to development of drug resistance in the human tumor clonogenic assay," *Cancer Chemother Pharmacol*, 15: pp. 208-213 (1985).
Matsubara et al, Clinical Significance of Insulin-Like Growth Factor Type 1 Receptor and Epidermal Growth Factor Receptor in Patients with Advanced Gastric Cancer, *Oncology*, 74:76-83 (2008).

* cited by examiner

*Primary Examiner* — Elly-Gerald Stoica
(74) *Attorney, Agent, or Firm* — Leydig, Voit & Mayer, Ltd.

(57) ABSTRACT

A method of preventing and/or treating a cancer, the method including co-administering a dual inhibitor of c-Met (hereinafter, 'c-Met inhibitor') and an IGF-1R inhibitor to a subject in need thereof and a use of IGF-1R as a marker for resistance to a c-Met inhibitor.

13 Claims, 9 Drawing Sheets
Specification includes a Sequence Listing.

FIG. 2

| Sensitivity | Sensitive | | | | Resistant | | | |
|---|---|---|---|---|---|---|---|---|
| Cell line | Hs746T | | SNU-5 | | SNU-668 | | YCC-11 | |
| Family | L3-1Y/IgG2_24hr | 0 ug/ml | 10 ug/ml | 0 ug/ml | 10 ug/ml | 0 ug/ml | 10 ug/ml | 0 ug/ml | 10 ug/ml |
| EGFR | EGF R | | | | | | | | |
| | ErbB2 | | | | | | | | |
| | ErbB4 | | | | | | | | |
| HGFR | HGF R | | | | | | | | |
| FGFR | FGF R3 | | | | | | | | |
| Tie | Tie-2 | | | | | | | | |
| Insulin | Insulin R | | | | | | | | |
| | IGF-1 R | | | | | | | | |
| | ALK | | | | | | | | |
| Axl | Axl | | | | | | | | |
| | Dtk | | | | | | | | |
| | Mer | | | | | | | | |
| NGFR | TrkA | | | | | | | | |
| EphR | EphA6 | | | | | | | | |
| | EphA7 | | | | | | | | |
| | EphA10 | | | | | | | | |
| - | DDR1 | | | | | | | | |
| - | RYK | | | | | | | | |

SEQUENCE LISTING

```
<160> NUMBER OF SEQ ID NOS: 113

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
1               5                   10                  15

Val Lys Gly
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
```

```
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15
Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
```

```
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
 1               5                  10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
  1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110
```

```
<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
             35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)
```

-continued

```
<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

<210> SEQ ID NO 26
```

```
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
1               5                   10                  15
```

Ala

```
<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32
```

Lys Ser Ser Arg Ser Leu Leu Ala Ser Gly Asn Gln Asn Asn Tyr Leu
 1               5                   10                  15

Ala

```
<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33
```

Lys Ser Ser His Ser Leu Leu Ala Ser Gly Asn Gln Asn Asn Tyr Leu
 1               5                   10                  15

Ala

```
<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34
```

Trp Ala Ser Lys Arg Val Ser
 1               5

```
<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35
```

Trp Gly Ser Thr Arg Val Ser
 1               5

```
<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36
```

Trp Gly Ser Thr Arg Val Pro
 1               5

```
<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone
```

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain
      of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc    60
cagtgtgagg tgaagctggt ggagtctgga ggaggcttgg tacagcctgg gggttctctg   120
agactctcct gtgcaacttc tgggttcacc ttcactgatt actacatgag ctgggtccgc   180
cagcctccag aaaggcact tgagtggttg ggttttatta gaaacaaagc taatggttac   240
acaacagagt acagtgcatc tgtgaagggt cggttcacca tctccagaga taattcccaa   300
agcatcctct atcttcaaat ggacaccctg agagctgagg acagtgccac ttattactgt   360
gcaagagata ctggtttgc ttactggggc caagggactc tggtcactgt ctctgcagct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccgtg tggtcagcgt cctcaccgtc ctgcaccagg actggctgaa tggcaaggag  1020
```

-continued

```
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain
      of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atgattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca gtccagtca gagtctttta    180 gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

```
<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |

| Ser | Leu | Arg | Leu | Ser | Cys | Ala | Ala | Ser | Gly | Phe | Thr | Phe | Thr | Asp | Tyr |
|---|---|---|---|---|---|---|---|---|---|---|---|---|---|---|---|
| | | 20 | | | | 25 | | | | | 30 | | | | |

| Tyr | Met | Ser | Trp | Val | Arg | Gln | Ala | Pro | Gly | Lys | Gly | Leu | Glu | Trp | Leu |
|---|---|---|---|---|---|---|---|---|---|---|---|---|---|---|---|
| | 35 | | | | | 40 | | | | | 45 | | | | |

| Gly | Phe | Ile | Arg | Asn | Lys | Ala | Asn | Gly | Tyr | Thr | Thr | Glu | Tyr | Ser | Ala |
|---|---|---|---|---|---|---|---|---|---|---|---|---|---|---|---|
| 50 | | | | | 55 | | | | | 60 | | | | | |

| Ser | Val | Lys | Gly | Arg | Phe | Thr | Ile | Ser | Arg | Asp | Asn | Ser | Lys | Asn | Ser |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Ala | Arg | Asp | Asn | Trp | Phe | Ala | Tyr | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser | Ala | Ser | Thr | Lys | Gly | Pro | Ser | Val | Phe | Pro | Leu |
|---|---|---|---|---|---|---|---|---|---|---|---|---|---|---|---|
| | | 115 | | | | | 120 | | | | | 125 | | | |

| Ala | Pro | Ser | Ser | Lys | Ser | Thr | Ser | Gly | Gly | Thr | Ala | Ala | Leu | Gly | Cys |
|---|---|---|---|---|---|---|---|---|---|---|---|---|---|---|---|
| 130 | | | | | 135 | | | | | 140 | | | | | |

| Leu | Val | Lys | Asp | Tyr | Phe | Pro | Glu | Pro | Val | Thr | Val | Ser | Trp | Asn | Ser |
|---|---|---|---|---|---|---|---|---|---|---|---|---|---|---|---|
| 145 | | | | | 150 | | | | | 155 | | | | | 160 |

| Gly | Ala | Leu | Thr | Ser | Gly | Val | His | Thr | Phe | Pro | Ala | Val | Leu | Gln | Ser |
|---|---|---|---|---|---|---|---|---|---|---|---|---|---|---|---|
| | | | | 165 | | | | | 170 | | | | | 175 | |

| Ser | Gly | Leu | Tyr | Ser | Leu | Ser | Ser | Val | Val | Thr | Val | Pro | Ser | Ser | Ser |
|---|---|---|---|---|---|---|---|---|---|---|---|---|---|---|---|
| | | | 180 | | | | | 185 | | | | | 190 | | |

| Leu | Gly | Thr | Gln | Thr | Tyr | Ile | Cys | Asn | Val | Asn | His | Lys | Pro | Ser | Asn |
|---|---|---|---|---|---|---|---|---|---|---|---|---|---|---|---|
| | | 195 | | | | | 200 | | | | | 205 | | | |

| Thr | Lys | Val | Asp | Lys | Lys | Val | Glu | Pro | Lys | Ser | Cys | Asp | Lys | Thr | His |
|---|---|---|---|---|---|---|---|---|---|---|---|---|---|---|---|
| | 210 | | | | | 215 | | | | | 220 | | | | |

| Thr | Cys | Pro | Pro | Cys | Pro | Ala | Pro | Glu | Leu | Leu | Gly | Gly | Pro | Ser | Val |
|---|---|---|---|---|---|---|---|---|---|---|---|---|---|---|---|
| 225 | | | | | 230 | | | | | 235 | | | | | 240 |

| Phe | Leu | Phe | Pro | Pro | Lys | Pro | Lys | Asp | Thr | Leu | Met | Ile | Ser | Arg | Thr |
|---|---|---|---|---|---|---|---|---|---|---|---|---|---|---|---|
| | | | | 245 | | | | | 250 | | | | | 255 | |

| Pro | Glu | Val | Thr | Cys | Val | Val | Val | Asp | Val | Ser | His | Glu | Asp | Pro | Glu |
|---|---|---|---|---|---|---|---|---|---|---|---|---|---|---|---|
| | | | 260 | | | | | 265 | | | | | 270 | | |

| Val | Lys | Phe | Asn | Trp | Tyr | Val | Asp | Gly | Val | Glu | Val | His | Asn | Ala | Lys |
|---|---|---|---|---|---|---|---|---|---|---|---|---|---|---|---|
| | | 275 | | | | | 280 | | | | | 285 | | | |

| Thr | Lys | Pro | Arg | Glu | Glu | Gln | Tyr | Asn | Ser | Thr | Tyr | Arg | Val | Val | Ser |
|---|---|---|---|---|---|---|---|---|---|---|---|---|---|---|---|
| | 290 | | | | | 295 | | | | | 300 | | | | |

| Val | Leu | Thr | Val | Leu | His | Gln | Asp | Trp | Leu | Asn | Gly | Lys | Glu | Tyr | Lys |
|---|---|---|---|---|---|---|---|---|---|---|---|---|---|---|---|
| 305 | | | | | 310 | | | | | 315 | | | | | 320 |

| Cys | Lys | Val | Ser | Asn | Lys | Ala | Leu | Pro | Ala | Pro | Ile | Glu | Lys | Thr | Ile |
|---|---|---|---|---|---|---|---|---|---|---|---|---|---|---|---|
| | | | | 325 | | | | | 330 | | | | | 335 | |

| Ser | Lys | Ala | Lys | Gly | Gln | Pro | Arg | Glu | Pro | Gln | Val | Tyr | Thr | Leu | Pro |
|---|---|---|---|---|---|---|---|---|---|---|---|---|---|---|---|
| | | | 340 | | | | | 345 | | | | | 350 | | |

| Pro | Ser | Arg | Glu | Glu | Met | Thr | Lys | Asn | Gln | Val | Ser | Leu | Thr | Cys | Leu |
|---|---|---|---|---|---|---|---|---|---|---|---|---|---|---|---|
| | | 355 | | | | | 360 | | | | | 365 | | | |

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Thr Asp Tyr
                20                  25                  30
Tyr Met Ser Trp Val Arg Gln Ala Pro Gly Lys Gly Leu Glu Trp Leu
            35                  40                  45
Gly Phe Ile Arg Asn Lys Ala Asn Gly Tyr Thr Thr Glu Tyr Ser Ala
     50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                85                  90                  95
Tyr Cys Ala Arg Asp Asn Trp Phe Ala Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
```

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

```
Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
 1               5                  10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Ser Tyr Ser Ala Pro Leu Thr Phe Gly Gly Gly Thr Lys Val Glu Ile
        100                 105                 110

Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Ser Tyr Ser Ala Pro Leu Thr Phe Gly Gln Gly Thr Lys Val Glu Ile
        100                 105                 110

Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
    130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215
```

```
<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg gctggagtg gttgggcttt attagaaaca agctaacgg ttacaccaca       180
gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa atgactcgag                                     1350
```

```
<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy
```

<400> SEQUENCE: 48

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca aagctaacgg ttacaccaca     180
gaatacagtg cgtctgtgaa aggcagattc accatctcaa gagataattc aaagaactca     240
ctgtatctgc aaatgaacag cctgcgtgct gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa atgactcgag                                      1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggctc actccgtttg      60
tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc caaaacacac     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
```

```
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag    1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc     60
atcaactgca gtccagcca gagtctttta gctagcggca accaaaataa ctacttagct    120
tggcaccagc agaaaccagg acagcctcct aagatgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                           669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

```
gatattgtga tgacccagac tccactctcc ctgcccgtca cccctggaga gccggcctcc     60
atctcctgca gtccagtca gagtctttta gctagtggca accaaaataa ctacttggcc    120
tggcacctgc agaagccagg gcagtctcca cagatgctga tcatttgggc atccactagg    180
gtatctggag tccagacagg gttcagtggc agtgggtcag gcactgattt cacactgaaa    240
atcagcaggg tggaggctga ggatgttgga gtttattact gccagcagtc ctacagcgct    300
```

```
ccgctcacgt tcggacaggg taccaagctg gagctcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaagt ctacgcctgc    600
gaagtcaccc atcagggcct gagctcgccc gtcacaaaga gcttcaacag gggagagtgt    660
tgactcgag                                                            669

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52
gacatcgtga tgacccagtc tccagactcc ctggctgtgt ctctgggcga gagggccacc     60
atcaactgca gtccagcca gagtcttta gctagcggca accaaaataa ctacttagct    120
tggtaccagc agaaaccagg acagcctcct aagctgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaagt ctacgcctgc    600
gaagtcaccc atcagggcct gagctcgccc gtcacaaaga gcttcaacag gggagagtgt    660
tgactcgag                                                            669

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53
gatatccaga tgacccagtc cccgagctcc ctgtccgcct ctgtgggcga tagggtcacc     60
atcacctgca gtccagtca gagtcttta gctagtggca accaaaataa ctacttggcc    120
tggcaccaac agaaaccagg aaaagctccg aaaatgctga ttatttgggc atccactagg    180
gtatctggag tcccttctcg cttctctgga tccgggtctg gacggatttt cactctgacc    240
atcagcagtc tgcagccgga agacttcgca acttattact gtcagcagtc ctacagcgct    300
ccgctcacgt tcggacaggg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaaagt ctacgcctgc    600
```

| gaagtcaccc atcagggcct gagctcgccc gtcacaaaga gcttcaacag gggagagtgt | 660 |
|---|---|
| tgactcgag | 669 |

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
 1               5                  10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

| gctagcgttt tagcagaagt tcaattggtt gaatctggtg gtggtttggt tcaaccaggt | 60 |
|---|---|
| ggttctttga gattgtcttg tgctgcttct ggttttactt tcaccgatta ttacatgtcc | 120 |
| tgggttagac aagctccagg taaaggtttg aatggttgg gtttcattag aaacaaggct | 180 |
| aacggttaca ctaccgaata ttctgcttct gttaagggta gattcaccat ttctagagac | 240 |
| aactctaaga caccttgta cttgcaaatg aactccttga gagctgaaga tactgctgtt | 300 |
| tattactgcg ctagagataa ttggtttgct tattgggtc aaggtacttt ggttactgtt | 360 |
| tcttctggcc tcgggggcct cggaggagga ggtagtggcg gaggaggctc cggtggatcc | 420 |
| agcggtgtgg gttccgatat tcaaatgacc caatctccat cttctttgtc tgcttcagtt | 480 |
| ggtgatagag ttaccattac ttgtaagtcc tcccaatctt tgttggcttc tggtaatcag | 540 |
| aacaattact ggcttggca tcaacaaaaa ccaggtaaag ctccaaagat gttgattatt | 600 |
| tgggcttcta ccagagtttc tggtgttcca tctagatttt ctggttctgg ttccggtact | 660 |
| gattttactt tgaccatttc atccttgcaa ccagaagatt tcgctactta ctactgtcaa | 720 |
| caatcttact ctgctccatt gactttggt caaggtacaa aggtcgaaat caagagagaa | 780 |
| ttcggtaagc ctatccctaa ccctctcctc ggtctcgatt ctacgggtgg tggtggatct | 840 |
| ggtggtggtg ttctggtgg tggtggttct caggaactga caactatatg cgagcaaatc | 900 |
| ccctcaccaa ctttagaatc gacgccgtac tctttgtcaa cgactactat tttggccaac | 960 |
| gggaaggcaa tgcaaggagt ttttgaatat tacaaatcag taacgtttgt cagtaattgc | 1020 |
| ggttctcacc cctcaacaac tagcaaaggc agccccataa acacacagta tgtttttga | 1080 |
| gtttaaac | 1088 |

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference

```
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata tttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactcctt gagagctgaa gatactgctg tttattactg cgctagagat aattggtttg     900
cttattgggg tcaaggtact ttggttactg tttcttctgg cctcggggc ctcggaggag     960 gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
```

```
aaccaggtaa agctccaaag atgttgatta tttgggcttc taccagagtt tctggtgttc      1200
catctagatt ttctggttct ggttccggta ctgattttac tttgaccatt tcatccttgc      1260
aaccagaaga tttcgctact tactactgtc aacaatctta ctctgctcca ttgacttttg      1320
gtcaaggtac aaaggtcgaa atcaagagag aattcggtaa gcctatccct aaccctctcc      1380
tcggtctcga ttctacgggt ggtggtggat ctggtggtgg tggttctggt ggtggtggtt      1440
ctcaggaact gacaactata tgcgagcaaa tcccctcacc aactttagaa tcgacgccgt      1500
actctttgtc aacgactact attttggcca acgggaaggc aatgcaagga gtttttgaat      1560
attacaaatc agtaacgttt gtcagtaatt gcggttctca cccctcaaca actagcaaag      1620
gcagccccat aaacacacag tatgtttttt gagtttaaac ccgctgatct gataacaaca      1680
gtgtagatgt aacaaaatcg actttgttcc cactgtactt ttagctcgta caaaatacaa      1740
tatacttttc atttctccgt aaacaacatg ttttcccatg taatatcctt ttctattttt      1800
cgttccgtta ccaactttac acatacttta tatagctatt cacttctata cactaaaaaa      1860
ctaagacaat tttaattttg ctgcctgcca tatttcaatt tgttataaat tcctataatt      1920
tatcctatta gtagctaaaa aaagatgaat gtgaatcgaa tcctaagaga attgggcaag      1980
tgcacaaaca atacttaaat aaatactact cagtaataac ctatttctta gcattttga      2040 cgaaatttgc tattttgtta gagtctttta caccatttgt ctccacacct ccgcttacat      2100
caacaccaat aacgccattt aatctaagcg catcaccaac attttctggc gtcagtccac      2160
cagctaacat aaaatgtaag ctctcggggc tctcttgcct tccaacccag tcagaaatcg      2220
agttccaatc caaaagttca cctgtcccac ctgcttctga atcaaacaag ggaataaacg      2280
aatgaggttt ctgtgaagct gcactgagta gtatgttgca gtcttttgga aatacgagtc      2340
ttttaataac tggcaaaccg aggaactctt ggtattcttg ccacgactca tctccgtgca      2400
gttggacgat atcaatgccg taatcattga ccagagccaa acatcctcc ttaggttgat      2460 tacgaaacac gccaaccaag tatttcggag tgcctgaact attttttatat gcttttacaa      2520 gacttgaaat tttccttgca ataaccgggt caattgttct ctttctattg ggcacacata      2580
taatacccag caagtcagca tcggaatcta gagcacattc tgcggcctct gtgctctgca      2640
agccgcaaac tttcaccaat ggaccagaac tacctgtgaa attaataaca gacatactcc      2700
aagctgcctt tgtgtgctta atcacgtata ctcacgtgct caatagtcac caatgccctc      2760
cctcttggcc ctctcctttt ctttttttcga ccgaatttct tgaagacgaa agggcctcgt      2820
gatacgccta ttttttatagg ttaatgtcat gataataatg gtttcttagg acggatcgct      2880
tgcctgtaac ttacacgcgc ctcgtatctt ttaatgatgg aataatttgg gaatttactc      2940
tgtgtttatt tattttatg ttttgtattt ggatttaga aagtaaataa agaaggtaga      3000
agagttacgg aatgaagaaa aaaaaataaa caaaggttta aaaaatttca acaaaaagcg      3060
tactttacat atatatttat tagacaagaa aagcagatta aatagatata cattcgatta      3120
acgataagta aaatgtaaaa tcacaggatt ttcgtgtgtg gtcttctaca cagacaagat      3180
gaaacaattc ggcattaata cctgagagca ggaagagcaa gataaaaggt agtatttgtt      3240
ggcgatcccc ctagagtctt ttacatcttc ggaaaacaaa aactatttt tctttaatttt      3300 ctttttttac tttctatttt taatttatat atttatatta aaaaatttaa attataatta      3360
tttttatagc acgtgatgaa aaggacccag gtggcacttt tcggggaaat gtgcgcggaa      3420
cccctatttg tttattttc taaatacatt caaatatgta tccgctcatg agacaataac      3480
cctgataaat gcttcaataa tattgaaaaa ggaagagtat gagtattcaa catttccgtg      3540
```

```
tcgcccttat tcccttttt  gcggcatttt gccttcctgt ttttgctcac ccagaaacgc   3600
tggtgaaagt aaaagatgct gaagatcagt tgggtgcacg agtgggttac atcgaactgg   3660
atctcaacag cggtaagatc cttgagagtt tcgccccga  agaacgtttt ccaatgatga   3720
gcacttttaa agttctgcta tgtggcgcgg tattatcccg tgttgacgcc gggcaagagc   3780
aactcggtcg ccgcatacac tattctcaga atgacttggt tgagtactca ccagtcacag   3840
aaaagcatct tacggatggc atgacagtaa gagaattatg cagtgctgcc ataaccatga   3900
gtgataacac tgcggccaac ttacttctga acgatcggag gaccgaag   gagctaaccg   3960 cttttttgca acatggggga tcatgtaa   ctcgccttga tcgttgggaa ccggagctga   4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
tggatgaacg aaatagacag atcgctgaga taggtgcctc actgattaag cattggtaac   4380
tgtcagacca agtttactca tatatacttt agattgattt aaaacttcat ttttaattta   4440
aaaggatcta ggtgaagatc cttttgata  atctcatgac caaaatccct taacgtgagt   4500
tttcgttcca ctgagcgtca gaccccgtag aaaagatcaa aggatcttct tgagatcctt   4560
tttttctgcg cgtaatctgc tgcttgcaaa caaaaaaacc accgctacca gcggtggttt   4620
gtttgccgga tcaagagcta ccaactcttt ttccgaaggt aactggcttc agcagagcgc   4680
agataccaaa tactgtcctt ctagtgtagc cgtagttagg ccaccacttc aagaactctg   4740
tagcaccgcc tacatacctc gctctgctaa tcctgttacc agtggctgct gccagtggcg   4800
ataagtcgtg tcttaccggg ttggactcaa gacgatagtt accggataag gcgcagcggt   4860
cgggctgaac ggggggttcg tgcacacagc ccagcttgga gcgaacgacc tacaccgaac   4920
tgagatacct acagcgtgag cattgagaaa gcgccacgct tcccgaaggg agaaaggcgg   4980
acaggtatcc ggtaagcggc agggtcggaa caggagagcg cacgagggag cttccagggg   5040
ggaacgcctg gtatctttat agtcctgtcg ggtttcgcca cctctgactt gagcgtcgat   5100
ttttgtgatg ctcgtcaggg gggccgagcc tatggaaaaa cgccagcaac gcggcctttt   5160
tacggttcct ggccttttgc tggccttttg ctcacatgtt ctttcctgcg ttatcccctg   5220
attctgtgga taaccgtatt accgcctttg agtgagctga taccgctcgc cgcagccgaa   5280
cgaccgagcg cagcgagtca gtgagcgagg aagcggaaga gcgcccaata cgcaaaccgc   5340
ctctccccgc gcgttggccg attcattaat gcagctggca cgacaggttt cccgactgga   5400
aagcgggcag tgagcgcaac gcaattaatg tgagttacct cactcattag gcaccccagg   5460
ctttacactt tatgcttccg gctcctatgt tgtgtggaat tgtgagcgga taacaatttc   5520
acacaggaaa cagctatgac catgattacg ccaagctcgg aattaaccct cactaaaggg   5580
aacaaaagct ggctagt                                                 5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtcagcagtc ctacagccgc ccgtacacgt tcggacaggg taccaaggtg | 420 |
| gagatcaaac gtacg | 435 |

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59

| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtgggcagtc ctacagccgt ccgctcacgt tcggacaggg taccaaggtg | 420 |
| gagatcaaac gtacg | 435 |

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60

| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |

```
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtcttta     180 gctagtggca accaaaataa ctacttggcc tggcaccaac agaaaccagg aaaagctccg    240
aaaatgctga tttatttggc atccactagg gtatctggag tcccttctcg cttctctgga    300
tccgggtctg gacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, U6-HC7 hinge and constant region of
      human IgG1

<400> SEQUENCE: 62

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
                305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata actggtttgc ttactggggc caagggactc tggtcaccgt ctcctcggct     420

```
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctggggggg accgtcagtc    780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggagga tgaccaag     1140 aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, human IgG2 hinge and constant region of
      human IgG1

<400> SEQUENCE: 64

Met Glu Trp Ser Trp Val Phe Leu Val Thr Leu Leu Asn Gly Ile Gln
1               5                   10                  15

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

| | | | | | | | | | | | |
|---|---|---|---|---|---|---|---|---|---|---|---|
| Ser | Gly | Ala | Leu | Thr | Ser | Gly | Val | His | Thr | Phe | Pro | Ala | Val | Leu | Gln |
| | | | 180 | | | | | 185 | | | | 190 | | | |
| Ser | Ser | Gly | Leu | Tyr | Ser | Leu | Ser | Ser | Val | Val | Thr | Val | Pro | Ser | Ser |
| | | 195 | | | | | 200 | | | | | 205 | | | |
| Ser | Leu | Gly | Thr | Gln | Thr | Tyr | Ile | Cys | Asn | Val | Asn | His | Lys | Pro | Ser |
| | 210 | | | | | 215 | | | | | 220 | | | | |
| Asn | Thr | Lys | Val | Asp | Lys | Lys | Val | Glu | Arg | Lys | Cys | Cys | Val | Glu | Cys |
| 225 | | | | | 230 | | | | | 235 | | | | | 240 |
| Pro | Pro | Cys | Pro | Ala | Pro | Glu | Leu | Leu | Gly | Gly | Pro | Ser | Val | Phe | Leu |
| | | | | 245 | | | | | 250 | | | | | 255 | |
| Phe | Pro | Pro | Lys | Pro | Lys | Asp | Thr | Leu | Met | Ile | Ser | Arg | Thr | Pro | Glu |
| | | | 260 | | | | | 265 | | | | | 270 | | |
| Val | Thr | Cys | Val | Val | Val | Asp | Val | Ser | His | Glu | Asp | Pro | Glu | Val | Lys |
| | | 275 | | | | | 280 | | | | | 285 | | | |
| Phe | Asn | Trp | Tyr | Val | Asp | Gly | Val | Glu | Val | His | Asn | Ala | Lys | Thr | Lys |
| | 290 | | | | | 295 | | | | | 300 | | | | |
| Pro | Arg | Glu | Glu | Gln | Tyr | Asn | Ser | Thr | Tyr | Arg | Val | Val | Ser | Val | Leu |
| 305 | | | | | 310 | | | | | 315 | | | | | 320 |
| Thr | Val | Leu | His | Gln | Asp | Trp | Leu | Asn | Gly | Lys | Glu | Tyr | Lys | Cys | Lys |
| | | | | 325 | | | | | 330 | | | | | 335 | |
| Val | Ser | Asn | Lys | Ala | Leu | Pro | Ala | Pro | Ile | Glu | Lys | Thr | Ile | Ser | Lys |
| | | | 340 | | | | | 345 | | | | | 350 | | |
| Ala | Lys | Gly | Gln | Pro | Arg | Glu | Pro | Gln | Val | Tyr | Thr | Leu | Pro | Pro | Ser |
| | | 355 | | | | | 360 | | | | | 365 | | | |
| Arg | Glu | Glu | Met | Thr | Lys | Asn | Gln | Val | Ser | Leu | Thr | Cys | Leu | Val | Lys |
| | 370 | | | | | 375 | | | | | 380 | | | | |
| Gly | Phe | Tyr | Pro | Ser | Asp | Ile | Ala | Val | Glu | Trp | Glu | Ser | Asn | Gly | Gln |
| 385 | | | | | 390 | | | | | 395 | | | | | 400 |
| Pro | Glu | Asn | Asn | Tyr | Lys | Thr | Thr | Pro | Pro | Val | Leu | Asp | Ser | Asp | Gly |
| | | | | 405 | | | | | 410 | | | | | 415 | |
| Ser | Phe | Phe | Leu | Tyr | Ser | Lys | Leu | Thr | Val | Asp | Lys | Ser | Arg | Trp | Gln |
| | | | 420 | | | | | 425 | | | | | 430 | | |
| Gln | Gly | Asn | Val | Phe | Ser | Cys | Ser | Val | Met | His | Glu | Ala | Leu | His | Asn |
| | | 435 | | | | | 440 | | | | | 445 | | | |
| His | Tyr | Thr | Gln | Lys | Ser | Leu | Ser | Leu | Ser | Pro | Gly | Lys | | | |
| | 450 | | | | | 455 | | | | | 460 | | | | |

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
consisting of heavy chain of huAbF46-H4-A1, human IgG2 hinge and
constant region of human IgG1

<400> SEQUENCE: 65

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
```

```
gctagagata actggtttgc ttactggggc aagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgccccc ctgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcagggaac    1320 gtcttctcat gctccgtgat gcatgaggct ctgcacaacc actacacgca gaagagcctc    1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, human IgG2 hinge and constant region of
      human IgG2

<400> SEQUENCE: 66

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn

```
            165                 170                 175
Ser Gly Ala Leu Thr Ser Gly Val His Thr Phe Pro Ala Val Leu Gln
        180                 185                 190

Ser Ser Gly Leu Tyr Ser Leu Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
                275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
                355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67
gaattcgccg ccaccatgga atggagctgg gtttttctcg taacactttt aaatggtatc    60
cagtgtgagg ttcagctggt ggagtctggc ggtggcctgg tgcagccagg ggctcactc    120 cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggg cgtttcacta agcagagaa taattccaaa    300 aacacactgt acctgcagat gaacagcctg cgtgctgagg acactgccgt ctattattgt    360
```

```
gctagagata actggtttgc ttactggggc caagggactc tggtcaccgt ctcctcggct    420
agcaccaagg gcccatcggt cttccccctg gcgccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                          1404

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light
      chain of huAbF46-H4-A1(H36Y) and human kappa constant region

<400> SEQUENCE: 68

Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
```

```
              165                 170                 175
Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and human kappa
      constant region

<400> SEQUENCE: 69
aattcactag tgattaattc gccgccacca tggattcaca ggcccaggtc ctcatgttgc     60
tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt cccttctcgc ttctctggat    300
ccgggtctgg gacggatttc actctgacca tcagcagtct gcagccggaa gacttcgcaa    360
cttattactg tcagcagtcc tacagccgcc gtacacgttc ggacagggt accaaggtgg    420 agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgcccctcc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                              758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light
      chain of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
```

```
                85                  90                  95
Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)
```

-continued

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain
      of anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)

```
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact tgagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata ctggtttgc ttactgggc caagggactc tggtcactgt ctctgcagct     420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                              1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
```

```
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga aaggtcact atgagctgca gtccagtca gagtctttta      180 gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78
atgaaggccc ccgctgtgct tgcacctggc atcctcgtgc tcctgtttac cttggtgcag      60
aggagcaatg gggagtgtaa agaggcacta gcaaagtccg agatgaatgt gaatatgaag     120
tatcagcttc ccaacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg gaacacccag attgtttccc atgtcaggac     300
tgcagcagca agccaatttt atcaggaggt gtttggaaag ataacatcaa catggctcta     360
gttgtcgaca cctactatga tgatcaactc attagctgtg gcagcgtcaa cagagggacc     420
tgccagcgac atgtctttcc ccacaatcat actgctgaca tacagtcgga ggttcactgc     480
```

```
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gtttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt tcacacaag aataatcagg    840 ttctgttcca taaactctgg attgcattcc tacatggaaa tgcctctgga gtgtattctc    900
acagaaaaga gaaaaagag atccacaaag aaggaagtgt taatatact tcaggctgcg    960 tatgtcagca agcctggggc ccagcttgct agacaaatag gagccagcct gaatgatgac    1020
attcttttcg gggtgttcgc acaaagcaag ccagattctg ccgaaccaat ggatcgatct    1080
gccatgtgtg cattccctat caaatatgtc aacgacttct caacaagat cgtcaacaaa    1140 aacaatgtga gatgtctcca gcattttac ggacccaatc atgagcactg ctttaatagg    1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa    1800 actagagttc tccttggaaa tgagagctgc accttgactt aagtgagag cacgatgaat    1860 acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caagcctttt    2460
ttcatgttag atgggatcct ttccaaatac tttgatctca tttatgtaca taatcctgtg    2520
tttaagcctt ttgaaaagcc agtgatgatc tcaatgggca atgaaatgt actggaaatt    2580 aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
```

```
atatcaacag cactgttatt actacttggg tttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctactatgt gaacgtaaaa    4080 tgtgtcgctc cgtatccttc tctgttgtca tcagaagata cgctgatga tgaggtggac    4140 acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
 1               5                  10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125
```

```
Leu Ser Ser Val Lys Asp Arg Phe Ile Asn Phe Val Gly Asn Thr
        130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45
```

```
Glu Glu Cys Leu Ser Gly Thr Trp Thr Gln Gln Ile Cys Leu Pro Ala
 50                  55                  60

Ile Tyr Lys Val Phe Pro Asn Ser Ala Pro Leu Glu Gly Gly Thr Arg
 65                  70                  75                  80

Leu Thr Ile Cys Gly Trp Asp Phe Gly Phe Arg Arg Asn Asn Lys Phe
                 85                  90                  95

Asp Leu Lys Lys Thr Arg Val Leu Leu Gly Asn Glu Ser Cys Thr Leu
             100                 105                 110

Thr Leu Ser Glu Ser Thr Met Asn Thr Leu Lys Cys Thr Val Gly Pro
         115                 120                 125

Ala Met Asn Lys His Phe Asn Met Ser Ile Ile Ser Asn Gly His
     130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                 165                 170                 175

Leu Thr Gly Asn Tyr Leu Asn Ser Gly Asn Ser Arg His Ile Ser Ile
             180                 185                 190

Gly Gly Lys Thr Cys Thr Leu Lys Ser Val Ser Asn Ser Ile Leu Glu
         195                 200                 205

Cys Tyr Thr Pro Ala Gln Thr Ile Ser Thr Glu Phe Ala Val Lys Leu
     210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                 245                 250                 255

Trp Trp Lys Glu Pro Leu Asn Ile Val Ser Phe Leu Phe Cys Phe Ala
             260                 265                 270

Ser Gly Gly Ser Thr Ile Thr Gly Val Gly Lys Asn Leu Asn Ser Val
         275                 280                 285

Ser Val Pro Arg Met Val Ile Asn Val His Glu Ala Gly Arg Asn Phe
     290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                 325                 330                 335

Ala Phe Phe Met Leu Asp Gly Ile Leu Ser Lys Tyr Phe Asp Leu Ile
             340                 345                 350

Tyr Val His Asn Pro Val Phe Lys Pro Phe Glu Lys Pro Val Met Ile
         355                 360                 365

Ser Met Gly Asn Glu Asn Val Leu Glu Ile Lys Gly Asn Asp Ile Asp
     370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                 405                 410                 415

Asp Leu Leu Lys Leu Asn Ser Glu Leu Asn Ile Glu Trp Lys Gln Ala
             420                 425                 430

Ile Ser Ser Thr Val Leu Gly Lys Val Ile Val Gln Pro Asp Gln Asn
         435                 440                 445

Phe Thr Gly
    450
```

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

```
Val His Phe Asn Glu Val Ile Gly Arg Gly His Phe Gly Cys Val Tyr
 1               5                  10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82

```
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgttttga cggaccagtc ctacattgat     540
gttttacctg agttcagaga ttcttacccc attaagtatg ccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccccctcat    1260
gtgaatttc tcctggactc ccatccagtg tctccagaag tgattgtgga gcatacatta    1320
aaccaaaatg gc                                                        1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
domain of c-Met

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca atgtgtgcg atcggaggaa tgcctgagcg ggacatggac tcaacagatc     180
tgtctgcctg caatctacaa ggttttccca aatagtgcac cccttgaagg agggacaagg     240
ctgaccatat gtggctggga ctttggattt cggaggaata taaatttga tttaaagaaa     300
actagagttc tccttggaaa tgagagctgc accttgactt aagtgagag cacgatgaat     360
acattgaaat gcacagttgg tcctgccatg aataagcatt caatatgtc cataattatt     420
tcaaatggcc acgggacaac acaatacagt acattctcct atgtggatcc tgtaataaca     480
agtatttcgc cgaaatacgg tcctatggct ggtggcactt acttactttt aactggaaat     540
tacctaaaca gtgggaattc tagacacatt tcaattggtg gaaaaacatg tactttaaaa     600
```

-continued

```
agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatctttta ttagtggtgg gagcacaata      780
acaggtgttg ggaaaaacct gaattcagtt agtgtcccga gaatggtcat aaatgtgcat      840
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagcctt ttgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

```
gtgcatttca atgaagtcat aggaagaggg cattttggtt gtgtatatca tgggactttg       60
ttggacaatg atggcaagaa aattcactgt gctgtgaaat ccttgaacag aatcactgac      120
ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggaga tcttcgaaat tcattcgaa atgagactca taatccaact      300
gtaaaagatc ttattggctt tggtcttcaa gtagccaaag gcatgaaata tcttgcaagc      360
aaaaagtttg tccacagaga cttggctgca agaaactgta tgctggatga aaaattcaca      420
gtcaaggttg ctgattttgg tcttgccaga gacatgtatg ataaagaata ctatagtgta      480
cacaacaaaa caggtgcaaa gctgccagtg aagtggatgg ctttggaaag tctgcaaact      540
caaaagttta ccaccaagtc agatgtgtgg tcctttggcg tgctcctctg ggagctgatg      600
acaagaggag ccccaccta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatcctttt ctgaactggt gtcccggata      780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg gagacatca                             939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met antibody

<400> SEQUENCE: 85

Asp Asn Trp Phe Ala Tyr Trp Gly Gln Gly Thr Leu Val

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
 1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
 1               5                  10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

-continued

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr 65                  70                  75                  80
Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
                35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
                35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly

```
                1               5                   10                  15
Asp Arg Val Thr Met Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

```
Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

```
Glu Pro Ser Cys Asp Lys His Cys Cys Pro Pro Cys Pro
 1               5                  10
```

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

```
Glu Pro Lys Ser Cys Asp Cys His Cys Pro Pro Cys Pro
 1               5                  10
```

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

```
Glu Arg Lys Cys Cys Val Glu Cys Pro Pro Cys Pro
```

-continued

```
<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60
```

-continued

```
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg
```

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                 20                  25                  30

Gly Asn Gln Asn Asn Tyr Leu Ala Trp Tyr Gln Gln Lys Pro Gly Lys
             35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 109
<211> LENGTH: 442
<212> TYPE: PRT
<213> ORGANISM: Artificial Sequence
<220> FEATURE:
<223> OTHER INFORMATION: Synthetic heavy chain of anti-c-Met antibody 1

<400> SEQUENCE: 109

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30
```

```
Tyr Met His Trp Val Arg Gln Ala Pro Gly Gln Gly Leu Glu Trp Met
    35                  40                  45
Gly Arg Val Asn Pro Asn Arg Gly Thr Thr Tyr Asn Gln Lys Phe
50                  55                  60
Glu Gly Arg Val Thr Met Thr Thr Asp Thr Ser Thr Ser Thr Ala Tyr
65                  70                  75                  80
Met Glu Leu Arg Ser Leu Arg Ser Asp Thr Ala Val Tyr Tyr Cys
                85                  90                  95
Ala Arg Ala Asn Trp Leu Asp Tyr Trp Gly Gln Gly Thr Thr Val Thr
                100                 105                 110
Val Ser Ser Ala Ser Thr Lys Gly Pro Ser Val Phe Pro Leu Ala Pro
                115                 120                 125
Cys Ser Arg Ser Thr Ser Glu Ser Thr Ala Ala Leu Gly Cys Leu Val
                130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Lys Thr Tyr Thr Cys Asn Val Asp His Lys Pro Ser Asn Thr Lys
                195                 200                 205
Val Asp Lys Arg Val Glu Ser Lys Tyr Gly Pro Pro Cys Pro Pro Cys
                210                 215                 220
Pro Ala Pro Glu Ala Ala Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser Gln Glu Asp Pro Glu Val Gln Phe Asn Trp
                260                 265                 270
Tyr Val Asp Gly Val Glu Val His Asn Ala Lys Thr Lys Pro Arg Glu
                275                 280                 285
Glu Gln Phe Asn Ser Thr Tyr Arg Val Val Ser Val Leu Thr Val Leu
                290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                325                 330                 335
Gln Pro Arg Glu Pro Gln Val Tyr Thr Leu Pro Pro Ser Gln Glu Glu
                340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
                370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                405                 410                 415
Val Phe Ser Cys Ser Val Met His Glu Ala Leu His Asn His Tyr Thr
                420                 425                 430
Gln Lys Ser Leu Ser Leu Ser Leu Gly Lys
                435                 440
```

```
<210> SEQ ID NO 110
<211> LENGTH: 215
<212> TYPE: PRT
<213> ORGANISM: Artificial Sequence
<220> FEATURE:
<223> OTHER INFORMATION: Synthetic light chain of anti-c-Met antibody 1

<400> SEQUENCE: 110

Asp Ile Gln Met Thr Gln Ser Pro Ser Leu Ser Ala Ser Val Gly
 1               5                  10                  15

Asp Arg Val Thr Ile Thr Cys Ser Val Ser Ser Val Ser Ser Ile
                20                  25                  30

Tyr Leu His Trp Tyr Gln Lys Pro Gly Lys Ala Pro Lys Leu Leu
            35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Asp Cys
    210                 215

<210> SEQ ID NO 111
<211> LENGTH: 446
<212> TYPE: PRT
<213> ORGANISM: Artificial Sequence
<220> FEATURE:
<223> OTHER INFORMATION: Synthetic heavy chain of anti-c-Met antibody 2

<400> SEQUENCE: 111

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Thr Ala Tyr
                20                  25                  30

Thr Met His Trp Val Arg Gln Ala Pro Gly Gln Gly Leu Asp Trp Met
            35                  40                  45

Gly Gly Ile Lys Pro Asn Asn Gly Leu Ala Asn Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Ser Glu Ile Thr Thr Glu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Cys His
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 112
<211> LENGTH: 218
<212> TYPE: PRT
<213> ORGANISM: Artificial Sequence
<220> FEATURE:
<223> OTHER INFORMATION: Synthetic light chain of anti-c-Met antibody 2

<400> SEQUENCE: 112

Asp Ile Val Leu Thr Gln Ser Pro Asp Ser Leu Ala Val Ser Leu Gly
1               5                   10                  15
```

```
Glu Arg Ala Thr Ile Asn Cys Arg Ser Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
 50                  55                  60

Arg Phe Ser Gly Ser Gly Ser Arg Thr Asp Phe Thr Leu Thr Ile Ser
 65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 113
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 113

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

COMBINATION THERAPY USING C-MET INHIBITOR AND IGF-1R INHIBITOR FOR C-MET INHIBITOR RESISTANT CANCERS

CROSS-REFERENCE TO RELATED APPLICATIONS

This application claims the benefit of Korean Patent Application No. 10-2014-0163792 filed on Nov. 21, 2014 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 143,800 byte ASCII (Text) file named "721848_ST25.TXT," created on Nov. 23, 2015.

BACKGROUND OF THE INVENTION

1. Field

Provided is a method of preventing and/or treating a cancer, the method including co-administering a c-Met inhibitor and an IGF-1R inhibitor to a subject in need thereof and a use of IGF-1R as a marker for resistance to a c-Met inhibitor.

2. Description of the Related Art

It has been shown that resistance to a drug having a specific target is more common compared to resistance to a drug having no specific target. In addition, it is also known that the indications on which a targeting drug has a therapeutic effect when it is treated alone are limited. Therefore, co-administration of two or more targeting drugs can maximize the therapeutic effect in a subject by overcoming resistance caused by exclusive treatment with only one of the targeting drugs, and by exhibiting a therapeutic effect for an indication in which one of the targeting drugs has no therapeutic effect. Such co-administration is expected to contribute to extending the scope of indications to be treated by target drugs and to overcoming resistance thereto.

Therefore, for more effective treatment of a disease, there remains a need to develop effective combination therapy targeting two or more targets.

BRIEF SUMMARY OF THE INVENTION

An embodiment provides a combination therapy targeting c-Met and IGF-1R.

Another embodiment provides a pharmaceutical composition for combination therapy for treating and/or preventing cancer, the composition including a c-Met inhibitor and an IGF-1R inhibitor, as active ingredients.

Another embodiment provides a kit for treating and/or preventing cancer, including a first pharmaceutical composition including a c-Met inhibitor, a second pharmaceutical composition including an IGF-1R inhibitor, and a package container.

Another embodiment provides a method of treating and/or preventing cancer, the method including co-administering a c-Met inhibitor and an IGF-1R inhibitor to a subject in need thereof.

Another embodiment provides a pharmaceutical composition for overcoming resistance to a c-Met inhibitor, the composition including an IGF-1R inhibitor.

Another embodiment provides a method of overcoming resistance to a c-Met inhibitor, the method including administering an IGF-1R inhibitor together with a c-Met inhibitor to a subject who has resistance to the c-Met inhibitor.

Another embodiment provides a marker for predicting and/or examining (monitoring) an effect of a c-Met inhibitor, including IGF-1R protein and/or nucleic acids (e.g., full-length DNA, cDNA or mRNA) encoding IGF-1R. The marker may be used for determining the presence or absence of resistance to a c-Met inhibitor.

Another embodiment provides a method for predicting and/or examining (monitoring) an effect of a c-Met inhibitor, including measuring a level of IGF-1R protein and/or nucleic acids (e.g., full-length DNA, cDNA or mRNA) encoding IGF-1R in a biological sample obtained from a subject. The method may be used for determining the presence or absence of resistance to a c-Met inhibitor.

BRIEF DESCRIPTION OF THE DRAWINGS

FIG. 2 is schematic view of the results of FIG. 1, wherein the degree of darkness is directly proportional to the level of expression.

DETAILED DESCRIPTION OF THE INVENTION

Figure 1:
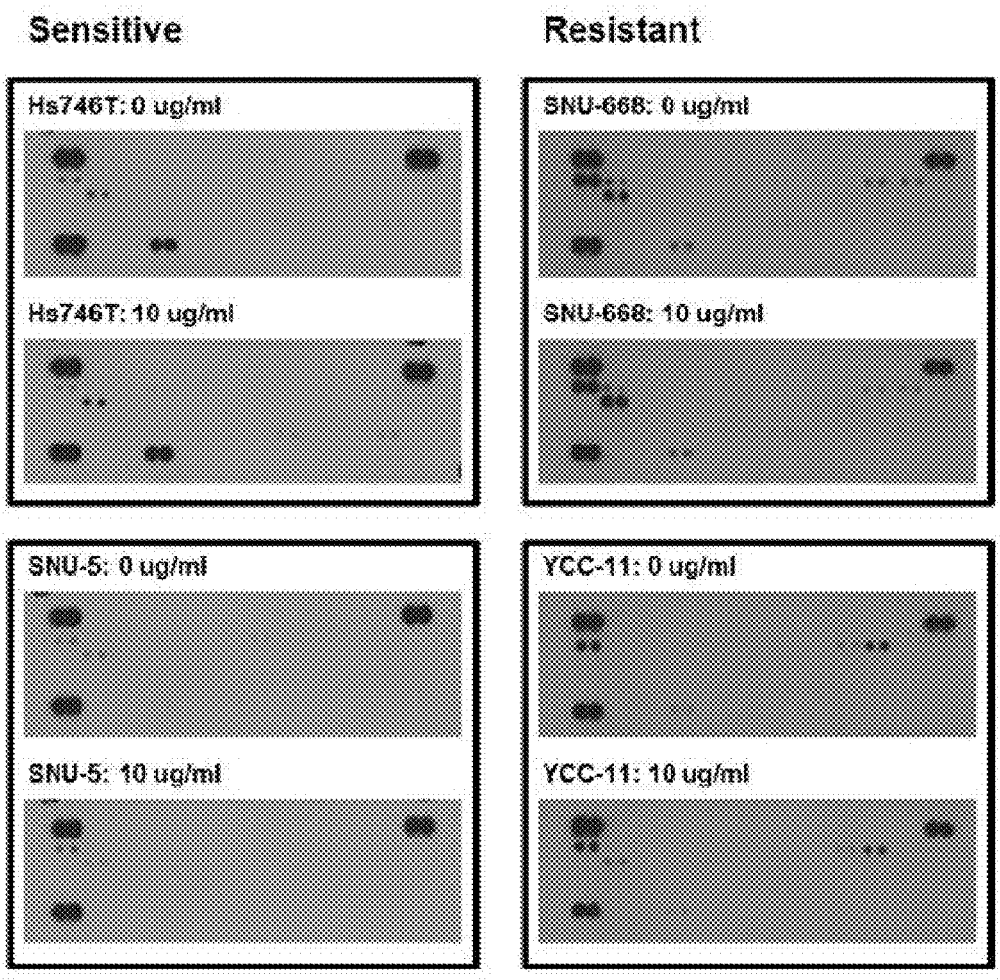
FIG. 1 displays immunoblotting results showing expression levels of receptor tyrosine kinases (RTKs; EGFR, ErbB2, HGFR (c-Met), and IGF-1R) in Hs746T and SNU-5 cell lines (anti-c-Met antibody sensitive) and SNU-668 and YCC-11 cell lines (anti-c-Met antibody resistant), wherein the lowest image is a reference indicating the positions of proteins.
Figure 1:
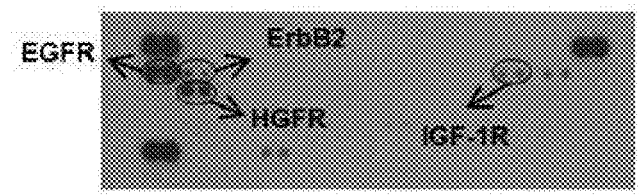

A c-Met inhibitor, such as an anti-c-Met antibody, generally exhibits strong anticancer effects on cancers having a high expression level of c-Met, such as gastric cancer, lung cancer, and the like. However, when resistance to an anti-c-Met antibody is inherently present in a subject (e.g., a c-Met resistant cancer cell) or acquired by repeated administration of the anti-c-Met antibody, the anti-c-Met antibody cannot exhibit its effect on the subject, even if the expression level of c-Met in the subject is high. In cells with a high level of c-Met expression which are resistant to an anti-c-Met antibody (e.g., does not exhibit its anticancer effect), the expression level of IGF-1R is considerably higher compared to cells on which an anti-c-Met antibody exhibits its effect (e.g., anticancer effect). Based thereon, IGF-1R can serve as a marker for determining the presence or absence of resistance to an anti-c-Met antibody and/or as a target for a drug for being co-administered together with an anti-c-Met antibody in a combination therapy.

By co-administering an anti-c-Met antibody and an IGFR1 inhibitor to simultaneously inhibit c-Met and IGF-1R, an anticancer effect can be achieved even in cases where such an effect cannot be obtained when only one of the targets is inhibited. Thus, the applicable scope of an anti-c-Met antibody can be expanded and resistance to an anti-c-Met antibody can be overcome.

Herein, the term "co-administration" and "combined administration" may be used interchangeably (i.e., have the same meaning).

The "c-Met" or "c-Met proteins" refer to receptor tyrosine kinases that bind to hepatocyte growth factors (HGF). The c-Met proteins may be those derived from all kinds of species, particularly a mammal, for example, those derived from a primate such as human c-Met (e.g. NP_000236.2), monkey c-Met (e.g., Macaca mulatta, NP_001162100), and the like, or those derived from a rodent such as mouse c-Met (e.g., NP_032617.2), rat c-Met (e.g., NP_113705.1), and the like. These proteins may include, for example, polypeptides encoded by the nucleotide sequence identified as GenBank Accession Number NM_000245.2, or proteins encoded by the polypeptide sequence identified as GenBank Accession Number NM_000236.2, or extracellular domains thereof. The receptor tyrosine kinase c-Met is involved in several mechanisms including cancer incidence, cancer metastasis, cancer cell migration, cancer cell penetration, angiogenesis, etc.

IGF-1R (insulin-like growth factor 1 receptor) binds to IGF1 (insulin-like growth factor 1) or IGF2 (insulin-like growth factor 2), and binds to insulin at a low affinity. The binding between IGF1 and IGF-1R increases the activity of receptor tyrosine kinases and induces auto-phosphorylation of the receptors or phosphorylation of internal related materials, thereby performing signal transduction. IGF-1R promotes proliferation of normal cells, but it can cause abnormal growth of cells. The overexpression of IGF-1R may cause formation of neoplasm, and thus its importance in cancer therapy emerged. The IGF-1R protein may be obtained from any species; for example, it may be at least one selected from the group consisting of human IGF-1R (e.g., AAI43722.1 (coding gene (cDNA or mRNA): BC143721.1), NP_000866.1 (coding gene (cDNA or mRNA): NM_000875.4), NP_001278787.1 (coding gene (cDNA or mRNA): NM_001291858.1)), etc.), mouse IGF-1R (e.g., AAI38870.1 (coding gene (cDNA or mRNA): BC138869.1), AA138869.1 (coding gene (cDNA or mRNA): BC138868.1), NP_034643.2 (coding gene (cDNA or mRNA): NM_010513.2), etc.), and the like, but not limited thereto.

It has been shown that IGF-1R signaling induces resistance to cytotoxic therapy and has a high relation with resistance to EGFR-targeting therapy. In particular, high expression of IGF-1R from cancer cells surgically excised from a gastric cancer patent is related to poor results of cancer therapy. In 86 gastric cancer patients having the surgical operation, the survival time is relatively longer for patients with low expression levels of IGF-1R and EGFR in the excised gastric cancer tissue compared to patients with high expression levels of IGF-1R and EGFR. Therefore, IGF-1R is considered as one of the important targets contributing to cancer cell growth through cross-talk with other RTKs.

As used herein, the term "c-Met inhibitor" may refer to any agent (e.g., a compound or composition) capable of inhibiting activity and/or expression of c-Met, or blocking c-Met signaling by inhibiting ligands thereof, thereby preventing, improving, alleviating, reducing, and/or treating a c-Met associated disease (e.g., a disease associating with abnormal activation and/or overexpression of c-Met, such as cancer) or its symptom. In addition, the c-Met inhibitor may refer to any substance capable of recognizing and/or binding to c-Met to degrade and/or inhibit the functions or expression thereof. For example, the c-Met inhibitor may be an anti-c-Met antibody which recognizes and/or binds to c-Met. The anti-c-Met antibody may bind to c-Met and induce internalization (into a cell) and degradation of c-Met.

As used herein, the term "effect of the c-Met inhibitor" may refer to an effect to prevent, improve, alleviate, reduce the severity of, and/or otherwise treat a c-Met associated disease, such as a cancer. For example, the effect of the c-Met inhibitor may refer to an effect of reducing (or inhibiting proliferation of) cancer cells or cancer tissues, killing cancer cells or cancer tissues, and/or inhibiting invasion and/or migration of cancer cells related to metastasis. Thus, the effect may refer to an anticancer effect such as inhibiting cancer cell proliferation, migration (metastasis), or invasion, or inducing cancer cell apoptosis, etc.

The present disclosure suggests a combination therapy by combined administration of a c-Met inhibitor and an IGF-1R inhibitor, having advantages to expand the scope of application of the c-Met inhibitor to indications (diseases) on which the c-Met inhibitor does not exhibit an effect when used alone, and overcome resistance to a c-Met inhibitor. The combined administration of the c-Met inhibitor and the IGF-1R inhibitor also leads to more effective treatment of a disease (e.g., cancer) upon which a c-Met inhibitor and/or IGF-1R inhibitor exhibits the effect even when each of them if used alone, i.e., a disease that is not resistant to a c-Met inhibitor. Also, by such combined administration, it is believed that the dose of each inhibitor can be reduced and/or the administration interval can be increase (i.e., the frequency of administration can be decreased), thereby reducing side effects in a subject to be administered with the inhibitors.

One embodiment provides a pharmaceutical composition for combination therapy for preventing and/or treating of a cancer, comprising or consisting essentially of a c-Met inhibitor and an IGF-1R inhibitor as active ingredients.

The pharmaceutical composition for combination therapy may be a mixed formulation (e.g., a single composition comprising two active ingredients) of a c-Met inhibitor and an IGF-1R inhibitor. The IGF-1R inhibitor and c-Met inhibitor may be included in any amount that is pharmaceutically effective when used together. The composition thus formulated can be used for simultaneous administration of the two active ingredients.

Alternatively, each of the c-Met inhibitor and the IGF-1R inhibitor can be formulated in a separate composition and the two active ingredients (or compositions) can be separately administered simultaneously or sequentially. For instance, a first pharmaceutical composition including a pharmaceutically effective amount of the IGF-1R inhibitor as an active ingredient and a second pharmaceutical composition including a pharmaceutically effective amount of the c-Met inhibitor as an active ingredient can be administered simultaneously or sequentially. In the case of the sequential administration, any order of administration may be used.

Another embodiment provides a kit useful for preventing and/or treating a cancer, comprising or consisting essentially of a first pharmaceutical composition including an IGF-1R inhibitor as an active ingredient, a second pharmaceutical composition including a c-Met inhibitor as an active ingredient, and a package container. The IGF-1R inhibitor and c-Met inhibitor may be used in amounts that are pharmaceutically effective when combined, which amount may be determined by the skilled medical practitioner or medical researcher. The package container can be any container that holds or otherwise links the two compositions in individual containers together in a single unit (e.g., a box that holds both containers, or plastic wrap that binds both containers together), or the package container may be a single, divided container having at least two chambers that each hold one of the two compositions.

A method of combination therapy for preventing and/or treating a cancer also is provided. The method comprises or consists essentially of co-administering a c-Met inhibitor and an IGF-1R inhibitor to a subject in need of the prevention and/or treatment of cancer. The IGF-1R inhibitor and c-Met inhibitor may be administered in amounts that are pharmaceutically effective when combined, which amount may be determined by the skilled medical practitioner or medical researcher. The method may further include, prior to the co-administration step, a step of identifying a subject in need of the prevention and/or treatment of cancer. The step of identifying may be conducted by any manners and/or methods known to the relevant field for identifying whether or not a subject needs the prevention and/or treatment of cancer. For example, the step of identifying may include diagnosing a subject to have a cancer, or identifying a subject who is diagnosed as a cancer subject, particularly a cancer associated with c-Met expression or a cancer exhibiting resistance to treatment with a c-Met inhibitor alone.

Co-administration may be conducted by administering the two active ingredients (i.e., c-Met inhibitor and IGF-1R inhibitor) simultaneously; for example, by administering a mixed formulation (e.g., single composition) of a c-Met inhibitor and an IGF-1R inhibitor, as described herein. Alternatively, the c-Met inhibitor and IGF-1R inhibitor can be administered separately. The co-administration may be conducted by a first step of administering a c-Met inhibitor, and a second step of administering an IGF-1R inhibitor, wherein the first and the second administration steps may be conducted simultaneously or sequentially. In case of the sequential administration, the first step and the second step may be performed in any order. In the sequential administration the first step and the second step may be separated by any suitable time interval (about 1 second to about 24 hours, about 1 second to about 12 hours, or about 1 second to about 60 minutes (e.g., about 1 second to about 10 minutes); or 1-60 seconds, 1-60 minutes, 1-24 hours, or 1-7 days, 1-14 days, 7-14 days, 1-30 days, or so on). The c-Met inhibitor and IGF-1R inhibitor may be administered in amounts that are pharmaceutically effective when combined, which amount may be determined by the skilled medical practitioner or medical researcher.

The term "the pharmaceutically effective amount" as used in this specification refers to an amount of which each active ingredient can exert pharmaceutically significant effects (e.g., an amount sufficient to prevent or treat cancer in a subject).

The subject for administration may be any animal, for example a mammal including a primate such as a human or a monkey, or a rodent such as a mouse or a rat, or a cell or tissue separated therefrom, or a culture of the cell or tissue. In particular, the subject may be a mammal including a primate such as a human or a monkey, or a rodent such as a mouse or a rat, or a cell or tissue separated therefrom, or a culture of the cell or tissue, who has an innate resistance or acquired resistance to a c-Met inhibitor when used alone.

By combined administration of a c-Met inhibitor and an IGF-1R inhibitor, a synergistic therapeutic effect can be achieved compared to administration of c-Met only or IGF-1R only. Furthermore, the increased therapeutic effect from the combined administration can be obtained even for a disease (e.g., a cancer) in which each of the inhibitors does not exhibit its effect or which has resistance to each of the inhibitors.

The IGF-1R inhibitor may refer to any drug capable of targeting and/or inhibiting IGF-1R protein or a nucleic acid (e.g., full-length DNA, cDNA or mRNA) encoding IGF-1R. In particular, the IGF-1R inhibitor may be at least one selected from the group consisting of a compound (small molecular compound or its pharmaceutically acceptable salt), a protein (e.g., an antibody, an antigen-binding fragment of antibody, etc.), a nucleic acid (e.g., an aptamer, siRNA, shRNA, microRNA, etc.) and the like, which targets and/or inhibit IGF-1R protein and/or nucleic acids (e.g., full-length DNA, cDNA or mRNA) encoding IGF-1R protein For example, the IGF-1R inhibitor may be at least one selected from the group consisting of linsitinib(OSI-906; 3-[8-Amino-1-(2-phenyl-7-quinolyl)imidazo[1,5-a]pyrazin-3-yl]-1-methyl-cyclobutanol), NVP-AEW541 (CAS#475489-16-8; 7-((1s,3s)-3-(azetidin-1-ylmethyl)cyclobutyl)-5-(3-(benzyloxy)phenyl)-7H-pyrrolo[2,3-d]pyrimidin-4-amine), GSK1904529A (CAS#1089283-49-7; N-(2,6-difluorophenyl)-5-(3-(2-(5-ethyl-2-methoxy-4-(4-(4-(methylsulfonyl)piperazin-1-yl)piperidin-1-yl)phenylamino)pyrimidin-4-yl)H-imidazo[1,2-a]pyridin-2-yl)-2-methoxybenzamide), NVP-ADW742 (CAS#475488-23-4; 5-(3-(benzyloxy)phenyl)-7-((1r,3r)-3-(pyrrolidin-1-ylmethyl)cyclobutyl)-7H-pyrrolo[2,3-d]pyrimidin-4-amine), BMS-536924 (CAS#468740-43-4; 4-[[(2S)-2-(3-chlorophenyl)-2-hydroxyethyl]amino]-3-[4-methyl-6-(4-morpholinyl)-1H-benzimidazol-2-yl]-2(1H)-pyridinone), figitumumab (CP-751,871), cixutumumab (IMC-A12), dalotuzumab (MK-0646), R1507 (fully human anti-IGF-1R antibody), XL-228 (CAS#898280-07-4), INSM-18 (nordihydroguaiaretic acid; NDGA; 4,4'-((2R,3S)-2,3-dimethylbutane-1,4-diyl)bis(benzene-1,2-diol)), BMS-754807 ((S)-1-(4-((5-cyclopropyl-1H-pyrazol-3-yl)amino)pyrrolo[2,1-f][1,2,4]triazin-2-yl)-N-(6-fluoropyridin-3-yl)-2-methylpyrrolidine-2-carboxamide), AG-1024 (Tyrphostin; CAS#65678-07-1; 2-(3-bromo-5-tert-butyl-4-hydroxybenzylidene)malononitrile), GSK1838705A (CAS#1116235-97-2; 2-(2-(1-(2-(dimethylamino)acetyl)-5-methoxyindolin-6-ylamino)-7H-pyrrolo[2,3-d]pyrimidin-4-ylamino)-6-fluoro-N-methylbenzamide), PQ 401 (CAS#196868-63-0; N-(5-Chloro-2-methoxyphenyl)-N'-(2-methyl-4-quinolinyl)urea), and pharmaceutically acceptable salts thereof, but not be limited thereto.

XL-228:

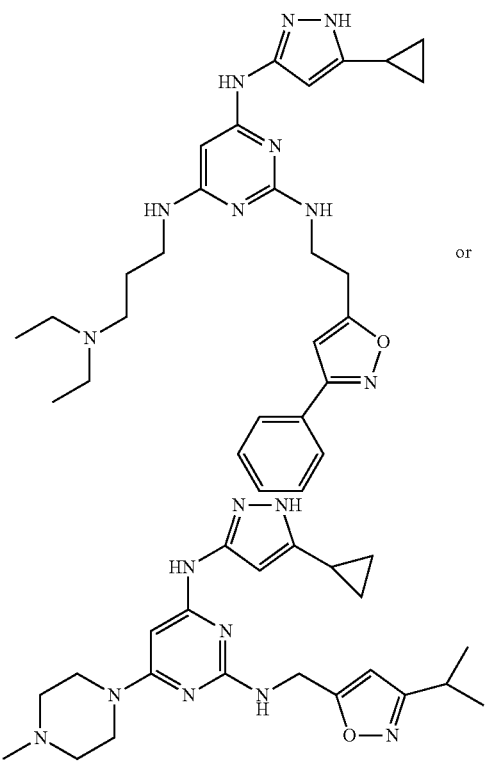

The c-Met inhibitor may be any drug targeting c-Met protein and/or nucleic acids (e.g., full-length DNA, cDNA or mRNA) encoding c-Met. In particular, c-Met inhibitor may be at least one selected from the group consisting of an antibody or an antigen-binding fragment thereof, an aptamer, siRNA, shRNA, microRNA, a compound (e.g., a small molecular compound or a pharmaceutically acceptable salt thereof), and the like, against (binding to or otherwise inhibiting) c-Met and/or a nucleic acid (e.g., full-length DNA, cDNA or mRNA) encoding c-Met.

For example, the c-Met inhibitor may be at least one selected from the group consisting of an anti-c-Met antibody or an antigen-binding fragment thereof, detailed below, crizotinib (PF-02341066; PF-02341066; 3-[(1R)-1-(2,6-dichloro-3-fluorophenyl)ethoxy]-5-(1-piperidin-4-ylpyrazol-4-yl)pyridin-2-amine), cabozantinib (XL-184; N-(4-(6,7-dimethoxyquinolin-4-yloxy)phenyl)-N-(4-fluorophenyl)cyclopropane-1,1-dicarboxamide), foretinib (N-(3-fluoro-4-(6-methoxy-7-(3-morpholinopropoxy)quinolin-4-yloxy)phenyl)-N-(4-fluorophenyl)cyclopropane-1,1-dicarboxamide), PHA-665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), SU11274((Z)—N-(3-chlorophenyl)-3-((3,5-dimethyl-4-(1-methylpiperazine-4-carbonyl)-1H-pyrrol-2-yl)methylene)-N-methyl-2-oxoindoline-5-sulfonamide), SGX-523(6-(6-(1-methyl-1H-pyrazol-4-yl)-[1,2,4]triazolo[4,3-b]pyridazin-3-ylthio)quinoline), PF-04217903(2-(4-(3-(quinolin-6-ylmethyl)-3H-[1,2,3]triazolo[4,5-b]pyrazin-5-yl)-1H-pyrazol-1-yl)ethanol), EMD 1214063(Benzonitrile, 3-[1,6-Dihydro-1-[[3-[5-[(1-Methyl-4-Piperidinyl)Methoxy]-2-PyriMidinyl]Phenyl]Methyl]-6-Oxo-3-Pyridazinyl]), golvatinib (N-(2-fluoro-4-((2-(4-(4-methylpiperazin-1-yl)piperidine-1-carboxamido)pyridin-4-yl)oxy)phenyl)-N-(4-fluorophenyl)cyclopropane-1,1-dicarboxamide), INCB28060(2-fluoro-N-methyl-4-(7-(quinolin-6-ylmethyl)imidazo[1,2-b][1,2,4]triazin-2-yl)benzamide), MK-2461(N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide), tivantinib (ARQ 197; (3R,4R)-3-(5,6-Dihydro-4H-pyrrolo[3,2,1-ij]quinolin-1-yl)-4-(1H-indol-3-yl)pyrrolidine-2,5-dione), NVP-BVU972(6-[[6-(1-Methyl-1H-pyrazol-4-yl)imidazo[1,2-b]pyridazin-3-yl]methyl]quinoline), AMG458({1-(2-hydroxy-2-methylpropyl)-N-[5-(7-methoxyquinolin-4-yloxy)pyridin-2-yl]-5-methyl-3-oxo-2-phenyl-2,3-dihydro-1H-pyrazole-4-carboxamide}), BMS 794833(N-(4-((2-amino-3-chloropyridin-4-yl)oxy)-3-fluorophenyl)-5-(4-fluorophenyl)-4-oxo-1,4-dihydropyridine-3-carboxamide), BMS 777607(N-[4-[(2-Amino-3-chloropyridin-4-yl)oxy]-3-fluorophenyl]-4-ethoxy-1-(4-fluorophenyl)-2-oxo-1,2-dihydropyridine-3-carboxamide), MGCD-265(N-(3-Fluoro-4-(2-(1-methyl-1H-imidazol-4-yl)thieno[3,2-b]pyridin-7-yloxy)phenylcarbamothioyl)-2-phenylacetamide), AMG-208(7-Methoxy-4-[(6-phenyl-1,2,4-triazolo[4,3-b]pyridazin-3-yl)methoxy]quinoline), BMS-754807((2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-pyrrolidinecarboxamide), JNJ-38877605(6-[Difluoro[6-(1-methyl-1H-pyrazol-4-yl)-1,2,4-triazolo[4,3-b]pyridazin-3-yl]methyl]quinoline), and pharmaceutically acceptable salts thereof.

The anti-c-Met antibody or an antigen-binding fragment thereof may be any type of antibody or antigen-binding fragment thereof, which is capable of specifically recognizing and/binding to c-Met. The antigen-binding fragment may be, for example, scFv, (scFv)2, scFvFc, Fab, Fab' or F(ab')2.

In one embodiment, the anti-c-Met antibody may be any antibody or antigen-binding fragment that acts on c-Met to induce intracellular internalization and degradation of c-Met. In another embodiment, the anti-c-Met antibody may be an antibody recognizing a specific region of c-Met, e.g., a region in the SEMA domain, as an epitope.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorin-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The anti-c-Met antibody used in accordance with the composition and method described herein may be an antibody that binds this region acts as an epitope.

The term "epitope" as used herein, refers to an antigenic determinant, a part of an antigen recognized by an antibody. In one embodiment, the epitope may be a region including about 5 or more contiguous amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti-c-Met antibody may specifically bind to an epitope which has about 5 to about 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence having about 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence having about 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 15, SEQ ID NO: 86, or an amino acid sequence having 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_5$ is Asn or Thr, Formula III
(SEQ ID NO: 6)
Asp-Asn-Trp-Leu-$Xaa_6$-Tyr, wherein $Xaa_6$ is Ser or Thr, Formula IV
(SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V
(SEQ ID NO: 8)
Trp-$Xaa_{11}$-Ser-$Xaa_{12}$-Arg-Val-$Xaa_{13}$ wherein $Xaa_{11}$ is Ala or Gly, $Xaa_{12}$ is Thr or Lys, and $Xaa_{13}$ is Ser or Pro, and Formula VI
(SEQ ID NO: 9)
$Xaa_{14}$-Gln-Ser-Tyr-Ser-$Xaa_{15}$-Pro-$Xaa_{16}$-Thr wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may comprise or consist essentially of:

a heavy chain variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85;

a light chain variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89; or a combination the heavy chain variable region and the light chain variable region.

In one embodiment, the anti-c-Met antibody or antigen-binding fragment may comprise or consist essentially of a heavy chain variable region comprising the amino acid sequence of SEQ ID NO: 17, 74, 87, 90, 91, 92, 93, or 94, a light chain variable region comprising the amino acid sequence of SEQ ID NO: 113, 18, 19, 20, 21, 75, 88, 95, 96, 97, 98, 99, or 107, or a combination of the heavy chain variable region and the light chain variable region.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include any of the antibodies defined in Korean Patent Publication No. 2011-0047698.

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

According to an embodiment, the anti-c-Met antibody may include a heavy chain including the amino acid sequence from the $18^{th}$ to $460^{th}$ positions of SEQ ID NO: 66 and a light chain including the sequence from the $21^{st}$ to $240^{th}$ positions of SEQ ID NO: 68, or a heavy chain including the amino acid sequence from the $18^{th}$ to $460^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The anti c-Met antibodies and antigen-binding fragments thereof may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic. The antibodies may be monoclonal.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "hinge region" as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody, or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In the anti-c-Met antibody, the portion of the light chain and the heavy chain excluding the CDRs, the light chain variable region, and the heavy chain variable region as defined above, for example the light chain constant region and the heavy chain constant region, may be those from any subtype of immunoglobulin (e.g., IgA, IgD, IgE, IgG (IgG1, IgG2, IgG3, IgG4), IgM, and the like).

The term "antigen-binding fragment" used herein refers to fragments of an intact immunoglobulin including portions of a polypeptide including at least one CDR or antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those having the amino acid length of about 1 to about 100, about 2 to about 50, particularly about 5 to about 25, and any kinds of amino acids may be included without any restriction.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

In the pharmaceutical composition (mixed formulation, first and second pharmaceutical compositions, etc.) or methods described herein, the active ingredients (a c-Met inhibitor or an IGF-1R inhibitor) may be provided (comprised or administered) along with at least one additive selected from the group consisting of a pharmaceutically acceptable carriers, diluents, and excipients.

The pharmaceutically acceptable carrier to be included in the composition or mixed formulation may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition or mixed formulation may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

The pharmaceutically effective amount of the pharmaceutical composition, the c-Met inhibitor, or the an IGF-1R inhibitor for a single dose may be prescribed in a variety of ways, depending on factors such as formulation methods, administration manners, age of subjects, body weight, gender, pathologic conditions, diets, administration time, administration interval, administration route, excretion speed, and reaction sensitivity. For example, the pharmaceutically effective amount of the IGF-1R inhibitor for a single dose may be in ranges of about 0.001 to about 100 mg/kg, or about 0.02 to about 10 mg/kg, and the pharmaceutically effective amount of the c-Met inhibitor for a single dose may be in ranges of about 0.001 to 100 mg/kg, or about 0.02 to about 10 mg/kg, but not limited thereto.

The term "pharmaceutically effective amount" used herein refers to an amount of the active ingredient (i.e., the c-Met inhibitor, or the an IGF-1R inhibitor) exhibiting effects in preventing or treating cancer, and may be properly determined in a variety of ways, depending on factors such as formulation methods, administration methods, age of patients, body weight, gender, pathologic conditions, diets, administration time, administration route, excretion speed, and reaction sensitivity.

The pharmaceutically effective amount for the single dose may be formulated into a single formulation in a unit dosage form or formulated in suitably divided dosage forms, or it may be manufactured to be contained in a multiple dosage container. For the kit, the pharmaceutically effective amount of the c-Met inhibitor and the pharmaceutically effective amount of the IGF-1R inhibitor for the single dose (one-time administration) may be each contained in a package container as a base unit.

The administration interval between the co-administrations that is defined as a period between the co-administration and the subsequent co-administration may be, but not limited to, 1-60 seconds, 1-60 minutes, 1-24 hours, 1-7 days, 1-14 days, 7-14 days, 1-30 days, or so on. In case that the co-administration comprises the sequential performance of the first administration step of administering the pharmaceutically effective amount of the c-Met inhibitor and the second administration step of administering the effective amount of the IGF-1R inhibitor, the administration may be simultaneous, or sequential with an interval between the first administration step and the second administration step of about 1 second to about 24 hours, about 1 second to about 12 hours, or about 1 second to about 60 minutes (e.g., about 1 second to about 10 minutes), and their administration may occur in any order.

The mixed formulation or the pharmaceutical compositions for co-administration may be a solution in oil or an aqueous medium, a suspension, a syrup, or an emulsifying solution form, or they may be formulated into a form of an extract, powders, granules, a tablet or a capsule, and they may further include a dispersing agent or a stabilizing agent for their formulation.

In embodiments where the c-Met inhibitor is an anti-c-Met antibody or an antigen binding fragment thereof, the pharmaceutically effective amount of the c-Met inhibitor as an active ingredient may be formulated into an immunoliposome. A liposome containing an antibody may be prepared using any methods well known in the pertinent field. The immunoliposome is a lipid composition including phosphatidylcholine, cholesterol, and polyethyleneglycol-derivated phosphatidylethanolamine, which may be prepared by a reverse phase evaporation method. For example, Fab' fragments of an antibody may be conjugated to the liposome through a disulfide-exchange reaction. A chemical drug, such as doxorubicin, may further be included in the liposome.

The pharmaceutical composition and method for co-administration proposed in this disclosure can be used for preventing and/or treating a cancer. The cancer may be a cancer related to or characterized by overexpression and/or abnormal activation of c-Met. The cancer may be a solid cancer or blood cancer. The cancer may be a c-Met inhibitor (e.g., an anti-c-Met antibody) non-effective cancer on which a c-Met inhibitor such as an anti-c-Met antibody has no anticancer effect when treated alone (i.e., the cancer is not responsive (susceptive) to treatment with a c-Met inhibitor in the absence of an IGF-1R inhibitor); as well as a cancer on which the c-Met inhibitor has anticancer effect when treated alone or which has no resistance to the c-Met inhibitor. The cancer that is not responsive (susceptive) to treatment with a c-Met inhibitor may have resistance to the c-Met inhibitor in the absence of an IGF-1R inhibitor in the absence of an IGF-1R inhibitor. For instance, the cancer may be, not limited to, at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, osteosarcoma and so on. In a particular embodiment, the cancer may a cancer having innate or acquired resistance to the c-Met inhibitor. In addition, the cancer may be one selected from gastric cancer, lung cancer, and the like, which have high expression of IGF-1R, but not be limited thereto. The cancer may be a primary cancer or a metastatic cancer.

The prevention and/or treatment effects of the cancer may include effects of not only inhibiting the growth of the cancer cells but also inhibiting the ability of the cancer to migrate, invade healthy cells, and metastasize.

Another embodiment provides partners for combination therapy capable of improving the effect of each other and overcoming resistance to each. In particular, provided is a use of an IGF-1R inhibitor as a partner drug for co-administration with a c-Met inhibitor, that is, the drug is suitable for use in a combination therapy using an c-Met inhibitor, and allows the c-Met inhibitor to exhibit the effect on a disease on which the c-Met inhibitor has no effect when it administered alone or disease having resistance to the c-Met inhibitor.

Therefore, an embodiment provides a pharmaceutical composition for improving the effect of a c-Met inhibitor, which comprises an IGF-1R inhibitor. Another embodiment provides a method for improving the effect of a c-Met inhibitor, comprising co-administering a c-Met inhibitor together with an IGF-1R inhibitor.

The term "improving the effect of a c-Met inhibitor" may comprise making the c-Met inhibitor to have an effect on a disease (e.g., a cancer) on which the c-Met inhibitor has no or only little effect when it is used alone and/or a disease (e.g., a cancer) having resistance to the c-Met inhibitor. Therefore, the composition or method for improving the effect of a c-Met inhibitor may a composition or method for overcoming (treating, reducing, and/or alleviating) resistance to the c-Met inhibitor.

Another embodiment provides a biomarker for predicting and/or monitoring an effect of a c-Met inhibitor, comprising at least one selected from the group consisting of IGF-1R protein and nucleic acids (full length DNA, cDNA, or mRNA) encoding IGF-1R. The nucleic acid encoding IGF-1R may be full length DNA, cDNA, or mRNA of nucleic acids (e.g., full-length DNA, cDNA or mRNA) encoding IGF-1R.

Another embodiment provides a composition or a kit for predicting and/or monitoring an effect of a c-Met inhibitor, comprising a material interacting with at least one selected from the group consisting of IGF-1R protein and nucleic acids encoding IGF-1R.

Another embodiment provides a method for predicting and/or monitoring an effect of a c-Met inhibitor, comprising measuring the level of at least one selected from the group consisting of IGF-1R protein and nucleic acids (full-length DNA, cDNA or mRNA) encoding IGF-1R in a biological sample from a subject (to be tested).

The term "predicting an effect of a c-Met inhibitor" may refer to predicting (determining) whether or not the c-Met inhibitor exhibit its effect on an individual subject by confirming a factor affecting the display of effect of the c-Met inhibitor, such as the presence/absence of innate (inherent) resistance to the c-Met inhibitor. When it is confirmed that a c-Met inhibitor exhibits an effect on an individual subject, the subject may be determined as a subject suitable for application of the c-Met inhibitor. Therefore, the biomarker, composition, kit, or method for predicting an effect of a c-Met inhibitor may be a biomarker, composition, kit, or method for selecting a subject for application of the c-Met inhibitor.

The term "monitoring an effect of a c-Met inhibitor" may refer to monitoring whether the c-Met inhibitor exhibits its effect well or not and/or resistance to the c-Met inhibitor is induced (acquired) by administration of the c-Met inhibitor or not. Therefore, the biomarker, composition, kit, or method for monitoring an effect of a c-Met inhibitor may be a biomarker, composition, kit, or method for monitoring induction (or acquisition) of resistance to the c-Met inhibitor in a subject administered with the c-Met inhibitor.

In an embodiment, provided is a method for predicting an effect of a c-Met inhibitor, selecting a subject for application of a c-Met inhibitor, monitoring an effect of a c-Met inhibitor, or monitoring induction (or acquisition) of resistance to a c-Met inhibitor. In the resistance, since an anti-c-Met antibody is comprised in the c-Met inhibitor, when a resistance to the anti-c-Met antibody exists, the c-Met inhibitor may lose its effect. Therefore, the resistance may refer to a resistance to treatment of a c-Met inhibitor and/or a resistance to treatment of an anti-c-Met antibody.

As described above, a high level of at least one selected from IGF-1R or nucleic acids encoding IGF-1R in a biological sample (e.g., cells, tissues, body fluid, etc.) obtained (separated) from a subject may indicate that the biological sample or the subject has resistance to an anti-c-Met antibody and/or a c-Met inhibitor. Therefore, in the method for predicting an effect of a c-Met inhibitor or selecting a subject for application of a c-Met inhibitor, when at least one selected from IGF-1R or nucleic acids encoding IGF-1R is absent or present at a low level, it can be determined (predicted) that the c-Met inhibitor will exhibit an effect well on the biological sample or the subject from which the biological sample is obtained, or that the biological sample or the subject from which the biological sample is suitable for application of the c-Met inhibitor. Thus, the method for predicting an effect of a c-Met inhibitor or selecting a subject for application of a c-Met inhibitor may further comprise, after the measuring step, determining (predicting) that the predicting an effect of a c-Met inhibitor, selecting a subject for application of a c-Met inhibitor, or the biological sample or the subject from which the biological sample is suitable for application of the c-Met inhibitor, when at least one selected from IGF-1R or nucleic acids encoding IGF-1R is absent (not detected or not measured) or present at a low level.

As used herein, the term "at least one selected from IGF-1R or nucleic acids encoding IGF-1R is present at a low level" may refer to that the level (amount) of at least one selected from IGF-1R or nucleic acids (e.g., full-length DNA, cDNA or mRNA) encoding IGF-1R in a biological sample (test sample) from a subject (to be tested) is lower than that of a reference sample. The reference sample may refer to a biological sample (e.g., cells, tissues, body fluid, etc.) on which the c-Met inhibitor does not exhibit its effect (for example, an anticancer effect such as inhibiting of cancer cell proliferation, migration (metastasis), or invasion, or inducing cancer cell apoptosis, etc.), or a biological sample (e.g., cells, tissues, body fluid, etc.) separated (obtained) from a subject on which the c-Met inhibitor does not exhibit its effect (for example, an anticancer effect such as inhibiting of cancer cell proliferation, migration (metastasis), or invasion, or inducing cancer cell apoptosis, etc.). For example, the reference sample may be at least one selected from the group consisting of, but not be limited to, H1373 (ATCC, CRL-5866) lung cancer cell line, HCC1806 (ATCC, CRL-2335) breast cancer cell line, Caki-1 (ATCC, HTB-46) renal cancer cell line, SKBR3 (ATCC, HTB-30) breast cancer cell line, BT474 (ATCC, HTB-20) breast cancer cell line, HT-29 (ATCC, HTB-38) colon cancer cell line, LoVo (ATCC, CCL-229) colon cancer cell line, HCT116 (ATCC, CCL-247) colon cancer cell line, SW620 (ATCC, CCL-227) colon cancer cell line, Ls174T (ATCC, CL-188) colon cancer cell line, and cell lines wherein resistance to an anti-c-Met antibody and/or resistance to a c-Met inhibitor is induced by repeated or continued administration of the anti-c-Met antibody and/or c-Met inhibitor.

The method for predicting an effect of a c-Met inhibitor or selecting a subject for application of a c-Met inhibitor may further comprise, after the measuring step and prior to the determining step (if it is comprised), comparing the level (amount) of at least one selected from IGF-1R or nucleic acids encoding IGF-1R in a biological sample (test sample) from a subject of interest (to be tested), with that of a reference sample as described above. For this, the method for predicting an effect of a c-Met inhibitor or selecting a subject for application of a c-Met inhibitor may further comprise, prior to the comparing step, measuring the level (amount) of at least one selected from IGF-1R or nucleic acids (e.g., full-length DNA, cDNA or mRNA) encoding IGF-1R in the reference sample.

The steps of measuring the level of at least one selected from IGF-1R or nucleic acids encoding IGF-1R in the biological sample and the reference sample are performed simultaneously or sequentially in any order.

Alternatively, if the IGF-1R level, which is determined by immunohistochemistry (IHC) using a conventional anti-IGF-1R-antibody (e.g., SAB4300359 (SIGMA), or G11 (Ventana; Catalog Number: 790-4346), etc.), is lower than +1, e.g., 0 or +1, it can be determined that IGF-1R is present at a low level or absent.

The method for predicting an effect of a c-Met inhibitor or selecting a subject for application of a c-Met inhibitor may further comprise, after the step of determining, administering a c-Met inhibitor (e.g., an anti-c-Met antibody or antigen-binding fragment thereof, etc.) to the selected subject, who has low level of IGF-1R as described above.

In another embodiment, a method for monitoring an effect of a c-Met inhibitor, comprising measuring the level (amount) of at least one selected from IGF-1R or nucleic acids (e.g., full-length DNA, cDNA or mRNA) encoding IGF-1R in a biological sample from a subject who is administered with the c-Met inhibitor (or after administration of a c-Met inhibitor). As described above, the method for monitoring an effect of a c-Met inhibitor includes monitoring whether resistance to an anti-c-Met antibody and/or a c-Met inhibitor is induced (acquired) or not.

In the method of monitoring an effect of a c-Met inhibitor, it can be determined that a c-Met inhibitor exhibits its effect (for example, an anticancer effect such as inhibiting of cancer cell proliferation, migration (metastasis), or invasion, or inducing cancer cell apoptosis, etc.) in the subject or resistance to the c-Met inhibitor is not induced in the subject, if the level (amount) of at least one selected from IGF-1R or nucleic acids encoding IGF-1R in a biological sample from the subject who is administered with the c-Met inhibitor (or after administration of a c-Met inhibitor) is equal to (maintained) or decreased compared to that of a biological sample from a subject who is not administered with the c-Met inhibitor (or before administration of a c-Met inhibitor). Alternatively, it can be also determined that a c-Met inhibitor does not exhibit its effect (for example, an anticancer effect such as inhibiting of cancer cell proliferation, migration (metastasis), or invasion, or inducing cancer cell apoptosis, etc.) in the subject or resistance to the c-Met inhibitor is induced in the subject, if the level (amount) of at least one selected from IGF-1R or nucleic acids encoding IGF-1R in a biological sample from the subject who is administered with the c-Met inhibitor (or after administration of a c-Met inhibitor) is increased compared to that of a biological sample from a subject who is not administered with the c-Met inhibitor (or before administration of a c-Met inhibitor).

Therefore, the measuring step of the method of monitoring an effect of a c-Met inhibitor may comprise measuring the levels (amount) of at least one selected from IGF-1R or nucleic acids (e.g., full-length DNA, cDNA or mRNA) encoding IGF-1R in a biological sample from a subject before and after the subject is administered with a c-Met inhibitor.

In addition, the method of monitoring an effect of a c-Met inhibitor may further comprise, after the measuring step, comparing the levels of at least one selected from IGF-1R or nucleic acids encoding IGF-1R in a biological sample from a subject before and after the subject is administered with a c-Met inhibitor, and/or determining that 1) the c-Met inhibitor exhibits its effect (for example, an anticancer effect such as inhibiting of cancer cell proliferation, migration (metastasis), or invasion, or inducing cancer cell apoptosis, etc.) in the subject, a resistance to the c-Met inhibitor is not induced (not acquired) in the subject, or the treatment using the c-Met inhibitor can be maintained to the subject, when the level of at least one selected from IGF-1R or nucleic acids encoding IGF-1R in a biological sample from the subject after administration of a c-Met inhibitor is equal to or decreased compared to that of a biological sample from a subject before administration of a c-Met inhibitor, and/or 2) the c-Met inhibitor does not exhibit its effect (for example, an anticancer effect such as inhibiting of cancer cell proliferation, migration (metastasis), or invasion, or inducing cancer cell apoptosis, etc.) in the subject, a resistance to the c-Met inhibitor is induced (acquired) in the subject, or the treatment using the c-Met inhibitor is stopped to the subject, when the level of at least one selected from IGF-1R or nucleic acids encoding IGF-1R in a biological sample from the subject after administration of a c-Met inhibitor is increased compared to that of a biological sample from a subject before administration of a c-Met inhibitor. The c-Met inhibitor may be an anti-c-Met antibody.

The method of monitoring an effect of a c-Met inhibitor may further comprise, after the step of determining, maintaining an administration of a c-Met inhibitor (e.g., an anti-c-Met antibody or antigen-binding fragment thereof, etc.), when it is determined that a c-Met inhibitor exhibits its effect (for example, an anticancer effect such as inhibiting of cancer cell proliferation, migration (metastasis), or invasion, or inducing cancer cell apoptosis, etc.) in the subject or resistance to the c-Met inhibitor is not induced in the subject.

In addition, as described above, when an IGF-1R inhibitor is co-administered with a c-Met inhibitor, the effect of the c-Met inhibitor can be improved (for example, resistance to an anti-c-Met antibody and/or a c-Met inhibitor can be overcome); and thus, even if at least one selected from the group consisting of IGF-1R and a nucleic acid encoding IGF-1R exists in a biological sample from a subject, a desired effect can be achieved by co-administration of an IGF-1R inhibitor and a c-Met inhibitor.

Therefore, another embodiment provides a method for predicting an effect of a combined administration of a c-Met inhibitor and an IGF-1R inhibitor, and/or selecting a patient for application of a combined administration of a c-Met inhibitor and an IGF-1R inhibitor, the method comprising measuring a level of at least one selected from the group consisting of IGF-1R and a nucleic acid encoding IGF-1R in a biological sample from a subject. As described above, the detection (presence) of at least one selected from the group consisting of IGF-1R and a nucleic acid encoding IGF-1R in a biological sample from a subject may indicate that the biological sample or the subject has innate (inherent) or acquired resistance to an anti-c-Met antibody and/or a c-Met inhibitor; however, co-administration of a c-Met inhibitor and an IGF-1R inhibitor can overcome such resistance, thereby achieving an increased therapeutic effect despite such resistance.

Therefore, the method for predicting an effect of a combined administration of a c-Met inhibitor and an IGF-1R inhibitor and/or selecting a subject for application of a combined administration of a c-Met inhibitor and an IGF-1R inhibitor, may further comprise predicting that the combined administration of a c-Met inhibitor and an IGF-1R inhibitor is effective on the biological sample or the subject from which the biological sample is obtained or determining that the biological sample or the subject from which the biological sample is obtained is suitable for application of the combined administration of a c-Met inhibitor and an IGF-1R inhibitor, if at least one selected from the group consisting of IGF-1R and a nucleic acid encoding IGF-1R is detected (present) in a biological sample from a subject. In an embodiment, the biological sample or biological sample or the subject from which the biological sample is obtained may have a resistance to an anti-c-Met antibody and/or a c-Met inhibitor, which is innate (inherently) or acquired by repeated administration of a c-Met inhibitor, wherein such innate (inherently) or acquired resistance to a c-Met inhibitor can be overcome by co-administration of the c-Met inhibitor together with an IGF-1R inhibitor.

The method for predicting an effect of a combined administration of a c-Met inhibitor and an IGF-1R inhibitor and/or selecting a subject for application of a combined administration of a c-Met inhibitor and an IGF-1R inhibitor, may further comprise, after the step of predicting or determining, co-administering a c-Met inhibitor (e.g., an anti-c-Met antibody or antigen-binding fragment thereof, etc.) and an IGF-1R inhibitor to the selected subject.

In the above described method for predicting or monitoring an effect of a c-Met inhibitor or a combined administration of a c-Met inhibitor and an IGF-1R inhibitor or selecting a subject for application of a c-Met inhibitor or a combined administration of a c-Met inhibitor and an IGF-1R inhibitor, the step of measuring the level of at least one selected from IGF-1R or nucleic acids encoding IGF-1R (e.g., the step of measuring the level of at least one selected from IGF-1R or nucleic acids encoding IGF-1R in a biological sample from a subject and a reference sample or in a biological sample from a subject before and after the subject is administered with a c-Met inhibitor may comprise i) applying (adding) an interacting material that interacts with at least one selected from the group consisting IGF-1R or nucleic acids (e.g., full-length DNA, cDNA or mRNA) encoding IGF-1R to the biological sample and/or a reference sample; and ii) quantitatively analyzing the resulting reaction mixture to determine a level (amount) of at least one selected from the group consisting of IGF-1R or nucleic acids (e.g., full-length DNA, cDNA or mRNA) encoding IGF-1R.

In an embodiment, prior to the step i), a step of providing a biological sample (and/or a reference sample) may be further performed. The step of providing a biological sample may comprise obtaining (isolating) a biological sample from a subject or obtaining a biological sample which has been isolated from a subject.

In step i), as will be further elucidated below, the interacting material may be at least one selected from the group consisting of compounds (a small molecular chemical; e.g., general label such as a fluorescent, a dye, etc.), proteins (antibodies, aptamers, etc.), nucleic acids (DNA, RNA, etc.), and the like, binding to IGF-1R or nucleic acids (e.g., full-length DNA, cDNA or mRNA) encoding IGF-1R. For example, the interacting material may be at least one selected from the group consisting of a compound, an antibody, an aptamer, all specifically binding to IGF-1R, and a nucleic acid (e.g., a primer, a probe, an aptamer, etc.) binding to a part or entirety of a nucleic acid (e.g., full-length DNA, cDNA or mRNA) encoding IGF-1R, and optionally, may be conjugated with a label, such as a fluorescent or a dye. The step i) may be configured to form a complex by applying (adding) the interacting material to the biological sample (and/or a reference sample).

In step ii), the reaction mixture may be a complex resulting from interaction (binding) between at least one selected from the group consisting of IGF-1R and a nucleic acid (e.g., full-length DNA, cDNA or mRNA) encoding IGF-1R and the interacting material, which can be obtained in step i). The quantitatively analyzing step may comprise quantifying the complex, the label conjugated to the complex, or the IGF-1R or the nucleic acid gene segregated from the complex after the isolation of the complex from the biological sample (and/or the reference sample). The quantitative analysis of IGF-1R may be performed by any general quantifying means of proteins, such as immunochromatography, immunohistochemistry, immunohistochemical staining, enzyme linked immunosorbent assay (ELISA), radioimmunoassay (RIA), enzyme immunoassay (EIA), fluorescence immunoassay (FIA), luminescence immunoassay (LIA), Western blotting, microarray, surface plasmon resonance (SPR), flow cytometry assay (e.g., Cytometric Bead Array (CBA) assay), Intracellular staining, Luminex assay, and the like, but not limited thereto. The quantitative analysis of nucleic acids (e.g., full-length DNA, cDNA or mRNA) encoding IGF-1R may be performed by any general quantifying means of genes (DNA or RNA), such as polymerase chain reaction (PCR; e.g., qPCR, RT-PCR, etc.), FISH (fluorescent in situ hybridization), microarray (e.g., mRNA microarray), and the like, but not limited thereto, which may use the interacting material such as a primer, a probe, or an aptamer, all capable of hybridizing (hybridizable) with a part or entirety of the nucleic acids encoding IGF-1R. In an embodiment, In one embodiment, the primer is designed to detect a fragment of successive base pairs out of the nucleic acid (full-length DNA, cDNA or mRNA) encoding IGF-1R, for example, a fragment of about 5 to about 2000 bp or about 5 to about 1000 bp, e.g., about 10 to about 1500 bp, about 10 to about 1000 bp, about 10 to about 500 bp, about 20 to about 200 bp, or about 50 to about 200 bp, and may be a pair of primers having nucleotide sequences which are respectively hybridizable with (e.g., complementary to) 3'- and 5'-terminal regions of the fragment, the region ranging in size from about 5 to about 100 bp, e.g., about 5 to about 50 bp, about 5 to about 30 bp, or about 10 to about 25 bp (that is, each of the primer pair comprises about 5 to about 100 nt, e.g., about 5 to about 50 nt, about 5 to about 30 nt, or about 10 to about 25 nt). The probe or the aptamer hybridizable with a part or entirety of the nucleic acid encoding IGF-1R may have a nucleotide sequence with a size from about 5 to about 2000 nt, from about 5 to about 1500 nt, from about 5 to about 1000 nt, from about 5 to about 500 nt, from about 5 to about 100 nt, from about 5 to about 50 nt, from about 5 to about 30 nt, or from about 5 to about 25 nt, which is hybridizable with (or complementary to) a fragment of the nucleic acid encoding IGF-1R. As used herein, the term "hybridizable" means pertaining to complementarily binding to a specific region of the nucleic acid, with a sequence complementarity of 80% or higher, e.g., 90% or higher, 95% or higher, 98% or higher, 99% or higher, or 100% between the primer, probe or aptamer and the nucleic acid region.

Considering that characteristic of the therapy using a c-Met inhibitor such as an anti-c-Met antibody, a high level expression of c-Met in a cancer cell can serve as an advantageous condition so that a c-Met inhibitor can more effectively exhibit its effect (e.g., an anticancer effect). Therefore, c-Met and/or nucleic acids (e.g., full-length DNA, cDNA or mRNA) encoding c-Met may be serve as a marker for predicting or monitoring an effect of a c-Met inhibitor or selecting a subject for application of a c-Met inhibitor, and it may be used alone or in combination with IGF-1R and/or nucleic acid encoding IGF-1R.

Therefore, the composition for predicting or monitoring an effect of a c-Met inhibitor or selecting a subject for application of a c-Met inhibitor may further comprise an interacting material that interacts with at least one selected from the group consisting of c-Met and nucleic acids encoding c-Met, in addition to an interacting material that interacts with IGF-1R and/or nucleic acid encoding IGF-1R as described above. The interacting material that interacts with c-Met and/or nucleic acid encoding c-Met may be at least one selected from the group consisting of compounds (a small molecular chemical), proteins (antibodies, aptamers, etc.), nucleic acids (DNA, RNA, etc.), and the like, binding to c-Met or nucleic acids (e.g., full-length DNA, cDNA or mRNA) encoding c-Met. For example, the interacting material may be at least one selected from the group consisting of a compound, an antibody, an aptamer, all specifically binding to c-Met, and a nucleic acid (e.g., a primer, a probe, an aptamer, etc.) binding to a part or entirety of a nucleic acid (e.g., full-length DNA, cDNA or mRNA) encoding c-Met, and optionally, may be conjugated with a label, such as a fluorescent or a dye.

The method for predicting or monitoring an effect of a c-Met inhibitor or selecting a subject for application of a c-Met inhibitor may further comprise measuring a level of c-Met protein or a gene thereof (e.g., full-length DNA, cDNA, mRNA) in the biological sample from a subject. The steps of measuring the level of c-Met and/or c-Met coding nucleic acid and measuring the level of at least one selected from the group consisting of IGF-1R and nucleic acid encoding IGF-1R may be performed simultaneously or sequentially in any order. Details of the measuring step are as described above. For example, a western blotting technique may be employed. In this regard, when a predetermined amount (e.g., about 10 µs) of proteins obtained from a biological sample (e.g., cancer cells or tissues) is loaded on SDS PAGE gel, transferred onto the membrane, and reacted with an anti-c-Met antibody, and then, exposed on ECL reaction for a certain time (e.g., about 30 sec), the detection of a band may indicate that a prerequisite for the c-Met inhibitor therapy is established. In another embodiment, if the c-Met level, which is determined by immunohistochemistry (IHC) using a tissue section (e.g., (Formalin-fixed paraffin-embedded tissues (FFPE), etc.) of a tumor tissue, is +2 or more, the tumor tissue can be determined that a c-Met inhibitor can exhibit its therapeutic efficacy thereon. In another embodiment, when a biological sample is found to have a c-Met mRNA level of about 12,000 or higher, about 13,000 or higher, or about 14,000 or higher, as measured by Affymetrix array (Affymetrix GeneChip Human Genome U133 Plus 2.0 array; using the primer set "203510_at"), a prerequisite for a c-Met inhibitor therapy may be established. Cancer cells characterized by a high expression level of c-Met include cells from lung cancer, breast cancer, brain cancer, stomach cancer, liver cancer, and kidney cancer. However, any cancer cell, although derived from different kinds, may be a target of the c-Met inhibitor therapy if it expresses a high level of c-Met according to personal characteristics of patients.

In another embodiment, a biological sample used in the method for predicting or monitoring the efficacy of a c-Met inhibitor or the method for selecting a subject suitable to the application of a c-Met inhibitor may be a tissue, a cell or body fluid (blood, serum, urine, saliva, etc.) which shows a high expression level of c-Met, for example, a c-Met level of about 12,000 or higher, about 13,000 or higher, or about 14,000 or higher, as measured by Affymetrix array (Affymetrix GeneChip Human Genome U133 Plus 2.0 array; using the primer set "203510_at").

As used herein, the term "subject (suitable) for the application of a c-Met inhibitor" means a patient to which a c-Met inhibitor therapy is applicable suitably, and the term "subject" may be selected from the group consisting of mammals, such as rodents, e.g., mice, rats, etc., and primates, e.g., humans, monkeys, etc., e.g., a cancer patient. The biological sample may be a patient itself (mammals, such as primates, e.g., humans, monkeys, etc., or rodents, e.g., mice, rats, etc.) or a cell, a tissue or body fluid (e.g., blood, serum, urine, saliva, etc.) isolated from the patient or artificially an artificial culture thereof. The biological sample may be a cell, blood, or a serum.

Another embodiment provides a method of treating and/or preventing a cancer comprising co-administering a c-Met inhibitor to a subject in need thereof. In the method of preventing and/or treating cancer, the subject may be one from whom a biological sample shows a low level (amount) of at least one selected from the group consisting of IGF-1R and a nucleic acid encoding IGF-1R compared to a reference sample, therein the term "low level" and "reference sample" are as described above. For example, the subject may be 1) selected by the above method for selecting a subject for the application of a combined administration of a c-Met inhibitor.

Another embodiment provides a method of treating and/or preventing a cancer comprising co-administering a c-Met inhibitor and an IGF-1R inhibitor to a subject in need thereof. In the method of preventing and/or treating cancer, the subject may be one from whom a biological sample shows the presence of at least one selected from the group consisting of IGF-1R and a nucleic acid encoding IGF-1R.

For example, the subject may be selected by the above method for selecting a subject for the application of a combined administration of a c-Met inhibitor and an IGF-1R inhibitor.

The method of treating and/or preventing a cancer may further comprise identifying (selecting) the subject for application of a c-Met inhibitor or application of a combined administration of a c-Met inhibitor and an IGF-1R inhibitor, wherein the detailed process can be performed referring to the method of selecting a subject described above. The c-Met inhibitor may be an anti-c-Met antibody.

In the above methods of treating and/or preventing a cancer, the c-Met inhibitor and/or the IGF-1R inhibitor may be administered at a pharmaceutically effective amount as described above.

For example, the method of treating and/or preventing a cancer may comprise:

identifying a subject for application of a c-Met inhibitor; and administering a c-Met inhibitor to the subject.

Alternatively, the method of treating and/or preventing a cancer may comprise:

identifying a subject for application of combined administration of a c-Met inhibitor and an IGF-1R inhibitor; and co-administering a c-Met inhibitor and an IGF-1R inhibitor to the subject.

Alternatively, the method of treating and/or preventing a cancer may comprise:

selecting a subject for application of a c-Met inhibitor by measuring the level of IGF-1R and/or nucleic acid encoding IGF-1R in a biological sample from a subject; and administering a c-Met inhibitor to the subject.

Alternatively, the method of treating and/or preventing a cancer may comprise:

selecting a subject for application of combined administration of a c-Met inhibitor and an IGF-1R inhibitor by measuring the level of IGF-1R and/or nucleic acid encoding IGF-1R in a biological sample from a subject; and administering a c-Met inhibitor and an IGF-1R inhibitor to the subject.

In the above methods of treating and/or preventing a cancer, the step of selecting a subject may be performed referring to the above descriptions.

EXAMPLES

Hereafter, the present invention will be described in detail by examples.

The following examples are intended merely to illustrate the invention and are not construed to restrict the invention.

Reference Example 1: Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, a second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFv Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 1, below.

TABLE 1

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was selected for the following examples, and name as L3-1Y-IgG2.

Example 1: Searching Biomarkers for Selecting Anti-c-Met Antibody Effective (Sensitive) Group and Anti-c-Met Antibody Non-Effective (Resistance) Group Expression levels of receptor tyrosine kinase proteins (RTKs) were measured in cell lines Hs746T(HTB-135, ATCC) and SNU-5(00005, KCLB), on which anti-c-Met antibody L3-1Y/IgG2 exhibits anticancer effect when used alone, and cell lines SNU-668(00668, KCLB) and YCC-11 (Yonsei University), on which anti-c-Met antibody L3-1Y/IgG2 does not exhibit anticancer effect when used alone.

In particular, each ($4\times10^6$ cells) of the cell lines were treated with 10 ug/ml of L3-1Y/IgG2, and then, lysed using lysis buffer 17 (Cat. No. 895943; provided in Human Phospho-RTK Array Kit), to obtain 300 UG of proteins. For comparison, each cell line without antibody treatment was used as a control and subjected to the same experiment as described above. The obtained proteins were diluted with a buffer provided in a kit (R&D ARY001B), incubated at 4° C. for 24 hours, and then analyzed using the chemiluminesnce buffer provided in the kit.

The obtained results are shown in FIG. 1. As shown in FIG. 1, the expression profiles of receptor tyrosine kinase proteins (RTKs) in the above 4 types of cell lines are different from each other. In particular, a considerable difference is observed between protein expression profiles in L3-1Y/IgG2 sensitive groups and L3-1Y/IgG2 resistance groups.

To more clearly confirm the protein expression profiles obtained in FIG. 1, the results of FIG. 1 were measured by Densitometry (GenePix Pro 4.1 software). The protein expression levels are shown in FIG. 2.

Figure 3:
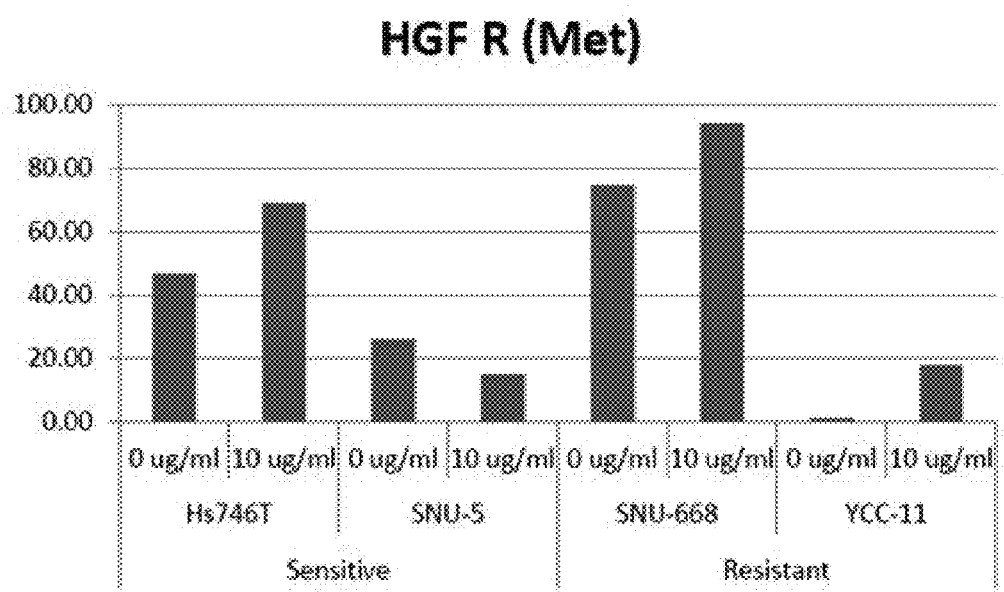
FIG. 3 is a graph showing the expression level of c-Met from the immunoblotting results shown in FIG. 1, wherein the expression level is obtained by normalizing the results (darkness and size of dots) shown in FIG. 1 with a positive control dot (which corresponds to a protein present on all membranes regardless of dose of antibody, and is used for normalizing RTKs expression to compare the expression between sample and membrane; loading control), and quantifying the relative value (%; intensity; mean pixel density) of darkness and size of c-Met corresponding dot comparing to that of the positive control dot (100%).
Figure 4:
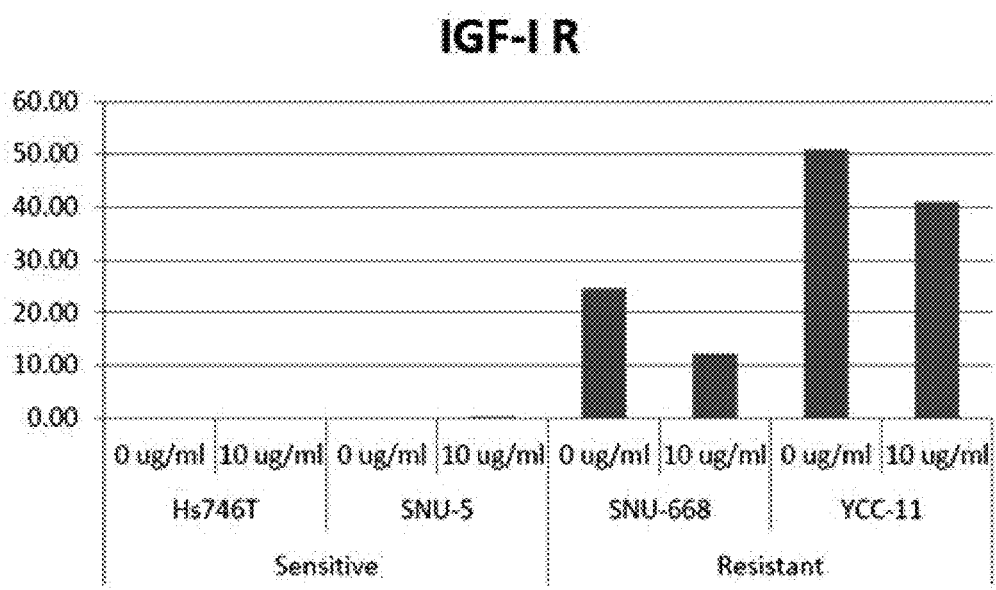
FIG. 4 is a graph showing the expression level of IGF-1R from the immunoblotting results shown in FIG. 1, wherein the expression level is obtained by normalizing the results (darkness and size of dots) shown in FIG. 1 with a positive control dot, and quantifying the relative value (%; intensity; mean pixel density) of darkness and size of IGF-1R corresponding dot comparing to that of the positive control dot (100%).
Figure 5:
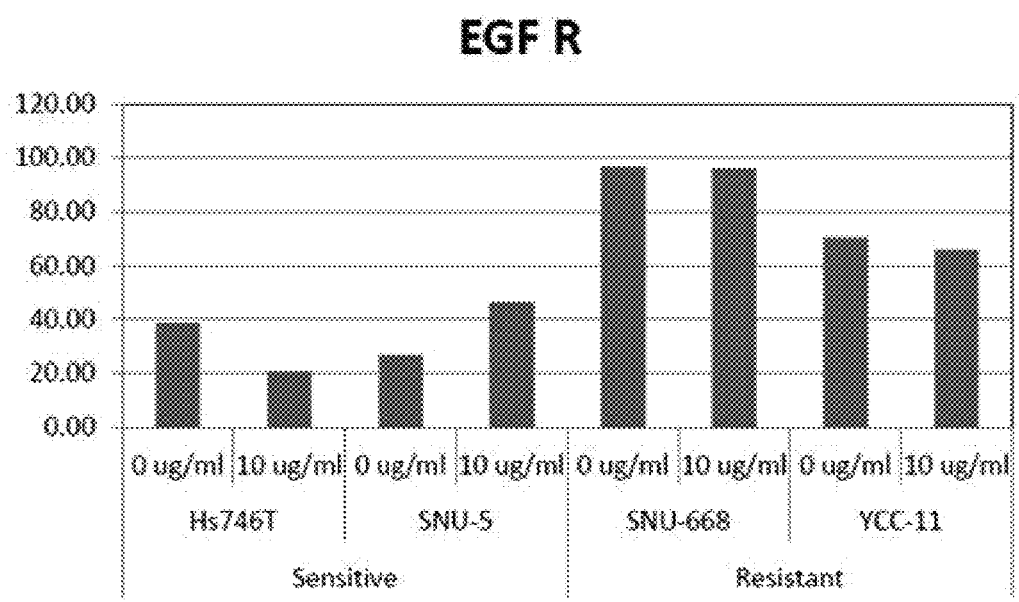
FIG. 5 is a graph showing the expression level of EGFR from the immunoblotting results shown in FIG. 1, wherein the expression level is obtained by normalizing the results (darkness and size of dots) shown in FIG. 1 with a positive control dot, and quantifying the relative value (%; intensity; mean pixel density) of darkness and size of EGFR corresponding dot comparing to that of the positive control dot (100%).
Figure 6:
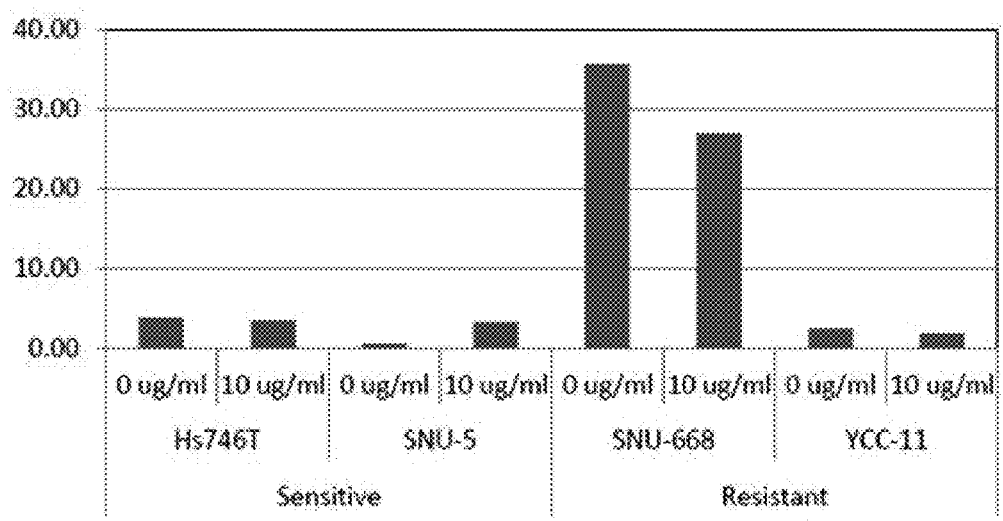
FIG. 6 is a graph showing the expression level of ErbB2 from the immunoblotting results shown in FIG. 1, wherein the expression level is obtained by normalizing the results (darkness and size of dots) shown in FIG. 1 with a positive control dot, and quantifying the relative value (%; intensity.

To more clearly confirm the protein expression level indicated in FIG. 2, the expression level of c-Met, IGF-1R, EGFR, and ErbB2 were quantified. In particular, pixels of densitometry (GenePix Pro 4.1 software) of dots were measured and a mean pixel density of each dot was calculated by considering the measured value of a positive dot (a control present on each membrane for normalization; Loading control) as 100%. The obtained quantification results are shown in FIG. 3 (c-Met), FIG. 4 (IGF-1R), FIG. 5 (EGFR), and FIG. 6 (ErbB2).

As shown in FIGS. 2-6, IGF-1R is not detected in L3-1Y/IgG2 sensitive groups, whereas it is detected in L3-1Y/IgG2 non-effective (resistance) groups at relatively high level. Therefore, IGF-1R was selected as a biomarker for determining (predicting or screening) effect of an anti-c-Met antibody.

Example 2: Examination of Effect of Co-Administration of an Anti-c-Met Antibody and an IGF-1R Inhibitor in Anti-c-Met Antibody Resistant Cancer Cells Anti-c-Met antibody resistance acquired gastric cancer cells, MKN45 re#1 and MKN45 re#24, were obtained by long term-administration of anti-c-Met antibody L3-1Y/IgG2 prepared in Reference Example 1 to MKN45 cells (JCRB 0254) on which anti-c-Met antibody L3-1Y/IgG2 exhibits its effect (e.g., cancer cell proliferation inhibition effect) when it is administered alone, and used for the following experiment.

In particular, in order to obtain anti-c-Met antibody resistant MKN45 gastric cancer cells, MKN45 gastric cancer cells were administered with L3-1Y/IgG2 for at least 3 months by increasing the administration concentration. The amount of L3-1Y/IgG2 administered was increased from 1 μg/ml to 10 μg/ml, until resistance to L3-1Y/IgG2 is induced. The obtained L3-1Y/IgG2 resistant clones were named as MKN45re#1 and MKN45re#24, respectively.

Figure 9:
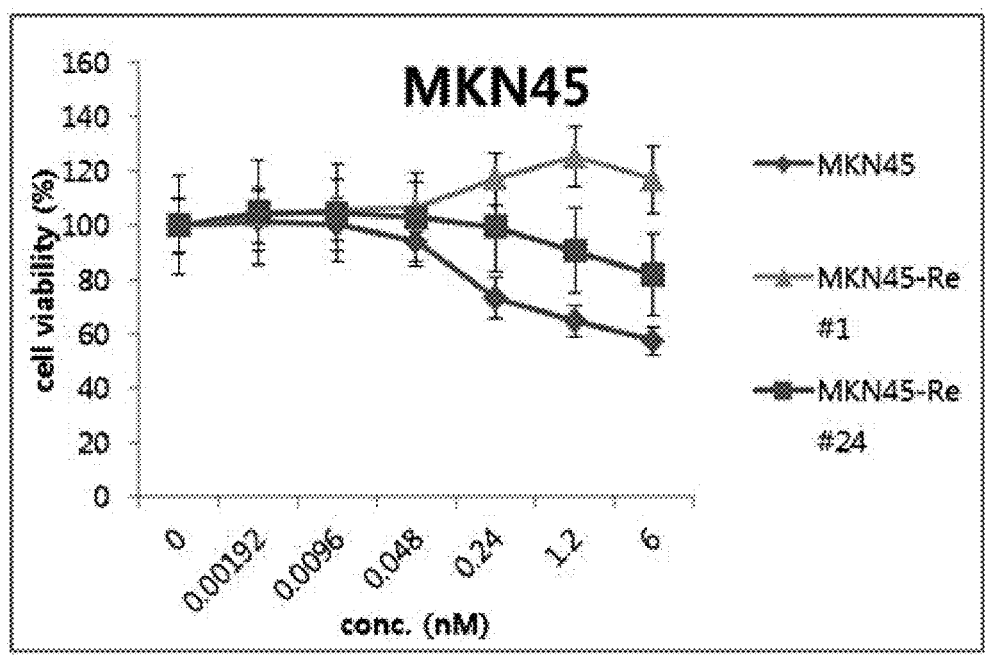
FIG. 9 is a graph showing the concentration dependent cell proliferation inhibition effect of anti-c-Met antibody L3-1Y/IgG2 in anti-c-Met antibody resistance induced cell lines MKN45 re#1 and MKN45 re#24, and non-resistant cell line MKN45.

In order to confirm the acquisition of resistance to L3-1Y/IgG2, the prepared L3-1Y/IgG2 resistant clones (MKN45 re#1 and MKN45 re#24) and MKN45 with no resistance were administered with various concentrations of L3-1Y/IgG2 (see FIG. 9). 72 hours after the antibody administration, the number of living cells was measured through CellTiter Glo assay (Promega, G7573). The obtained results are shown in FIG. 9. As shown in FIG. 9, the proliferation of MKN45 re#1 and MKN45 re#24 is not inhibited by treatment of L3-1Y/IgG2 even when the concentration of L3-1Y/IgG2 is increased, indicating that MKN45 re#1 and MKN45 re#24 acquire resistance to L3-1Y/IgG2.

The prepared L3-1Y/IgG2 resistance induced cell lines MKN45re#1 and MKN45re#24 were co-administered with L3-1Y/IgG2 and an IGF-1R inhibitor, to examine changes in cell proliferation of the L3-1Y/IgG2 resistance induced cell lines. Each of the L3-1Y/IgG2 resistant MKN45re#1 and MKN45re#24 cell lines was seeded on a 96-well plate at the amount of 10000 cells/well (medium: RPMI (GIBCO); culture conditions: 5% $CO_2$ and 37° C.), and on the next day, treated with L3-1Y/IgG2 (2 μg/ml) and linsitinib (10 uM) together. 72 hours after the co-treatment, the number of living cells was counted by CellTiter Glo assay (Promega, G7573). For comparison, the same experiments were conducted using a control group with no treatment of L3-1Y/IgG or linsitinib, a group treated with L3-1Y/IgG (2 μg/ml) only, and a group treated with linsitinib (10 uM) only.

Figure 7:
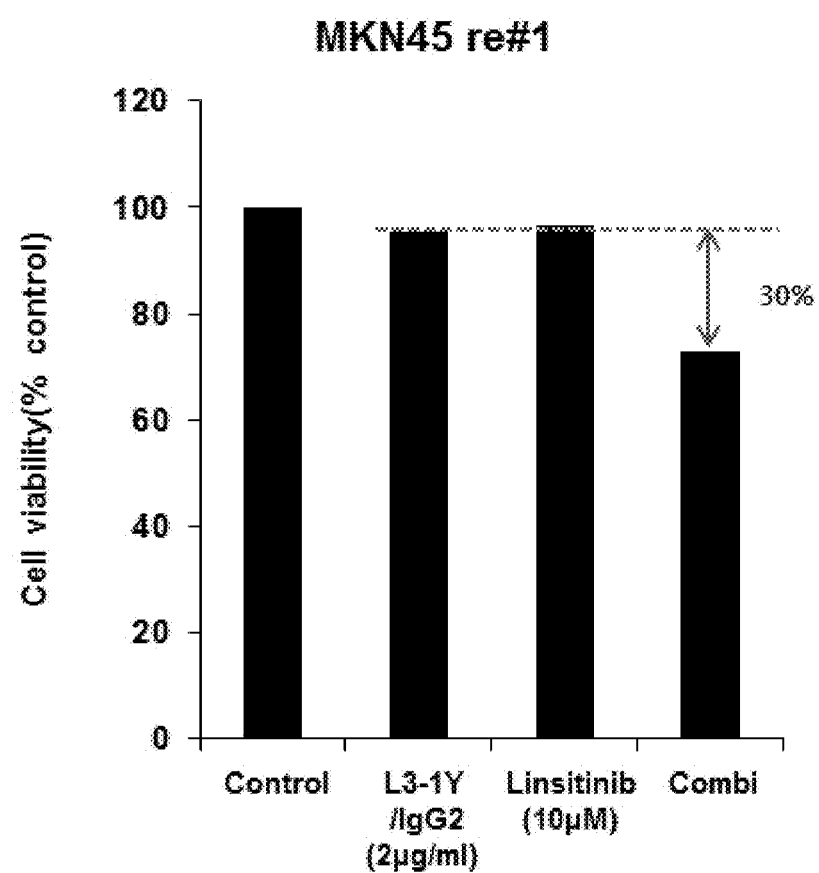
FIG. 7 is a graph showing cell proliferation inhibition effects of administration of anti-c-Met antibody L3-1Y/IgG2 alone, IGF-1R inhibitor linsitinib alone, and a combination of L3-1Y/IgG2 and linsitinib, in anti-c-Met antibody resistance induced cell line MKN45 re#1.
Figure 8:
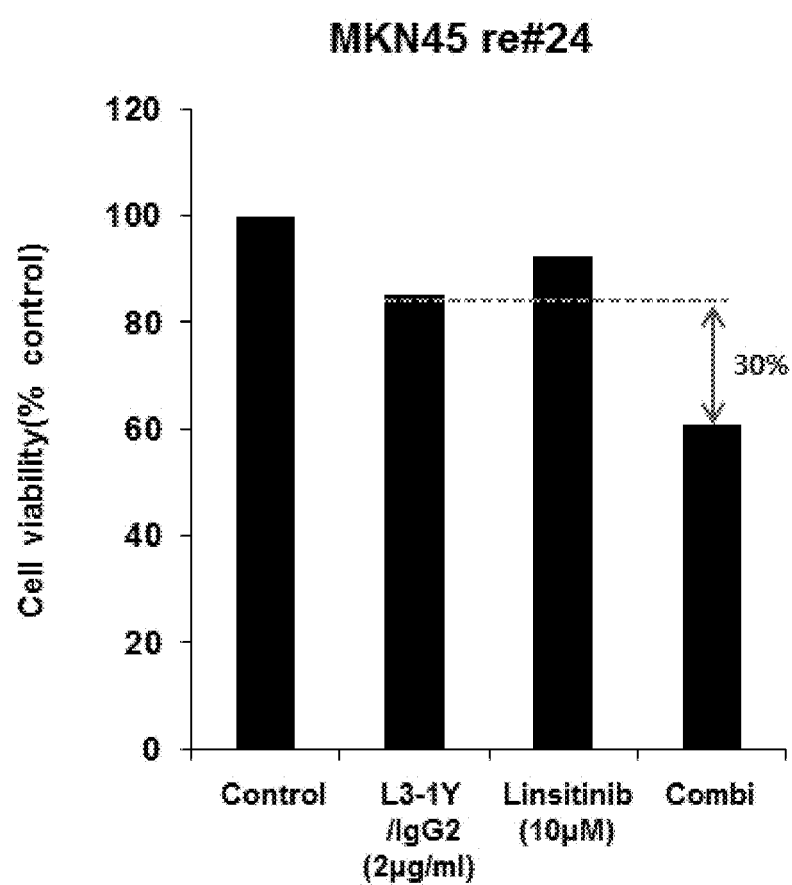
FIG. 8 is a graph showing cell proliferation inhibition effects of administration of anti-c-Met antibody L3-1Y/IgG2 alone, IGF-1R inhibitor linsitinib alone, and a combination of L3-1Y/IgG2 and linsitinib, in anti-c-Met antibody resistance induced cell line MKN45 re#24.

The obtained results are shown in FIGS. 7 and 8. As shown in FIGS. 7 and 8, when the L3-1Y/IgG2 resistance-induced MKN45 cell lines MKN45 re#1 and MKN45 re#24 were treated with L3-1Y/IgG2 only or linsitinib only, no cell proliferation inhibition effect is observed, whereas they were treated with L3-1Y/IgG2 and linsitinib together, clear and considerable cell proliferation inhibition effect (30% or more) is observed. These results suggest that by administration of an anti-c-Met antibody (L3-1Y/IgG2) together with an IGF-1R inhibitor (linsitinib), the scope of indications (disease), on which the anti-c-Met antibody can exhibit anticancer effect, can be expanded to those having resistance to the anti-c-Met antibody.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a cancer in a subject, or overcoming resistance to a c-Met inhibitor in a subject, the method comprising co-administering a pharmaceutically effective amount of a c-Met inhibitor and an insulin-like growth factor 1 receptor (IGF-1R) inhibitor to the subject, wherein the cancer is not responsive to treatment with the c-Met inhibitor in the absence of an IGF-1R inhibitor.

2. The method of claim 1, wherein the c-Met inhibitor and an IGF-1R inhibitor are co-administered in a single, mixed formulation, or each of the c-Met inhibitor and an IGF-1R inhibitor are administered in separate compositions, simultaneously or sequentially in any order.

3. The method of claim 1, wherein the c-Met inhibitor comprises at least one selected from the group consisting of an anti-c-Met antibody or an antigen-binding fragment thereof, an aptamer, siRNA, shRNA, microRNA, a small-molecule c-Met inhibitor or a pharmaceutically acceptable salt thereof.

4. The method of claim 1, wherein the c-Met inhibitor is an anti-c-Met antibody or an antigen-binding fragment thereof that comprises:

a heavy chain variable region comprising a CDR-H1 comprising SEQ ID NO: 1, a CDR-H2 comprising SEQ ID NO: 2, and a CDR-H3 comprising SEQ ID NO: 3; and a light chain variable region comprising a CDR-L1 comprising SEQ ID NO: 10, a CDR-L2 comprising SEQ ID NO: 11, and a CDR-L3 comprising SEQ ID NO: 12, 13, 14, 15, or 16;

or a heavy chain variable region comprising a CDR-H1 comprising SEQ ID NO: 1, a CDR-H2 comprising SEQ ID NO: 2, and a CDR-H3 comprising SEQ ID NO: 3, and a light chain variable region comprising a CDR-L1 comprising SEQ ID NO: 106, a CDR-L2 comprising SEQ ID NO: 11, and a CDR-L3 comprising SEQ ID NO: 13.

5. The method of claim 4, wherein the anti-c-Met antibody or an antigen-binding fragment thereof comprises:

a heavy chain variable region comprising SEQ ID NO: 17; and a light chain variable region comprising SEQ ID NO: 113, 18, 19, 20, 21, or 107.

6. The method of claim 4, wherein the anti-c-Met antibody comprises:

(1) a heavy chain comprising an amino acid sequence from the 18th to 462nd positions of SEQ ID NO: 62, and a light chain comprising an amino acid sequence from the 21st to 240th positions of SEQ ID NO: 68;

(2) a heavy chain comprising an amino acid sequence from the 18th to 461st positions of SEQ ID NO: 64, and a light chain comprising an amino acid sequence from the 21st to 240th positions of SEQ ID NO: 68;

(3) a heavy chain comprising an amino acid sequence from the 18th to 460th positions of SEQ ID NO: 66, and a light chain comprising an amino acid sequence from the 21st to 240th positions of SEQ ID NO: 68;

(4) a heavy chain comprising an amino acid sequence from the 18th to 462nd positions of SEQ ID NO: 62, and a light chain comprising an amino acid sequence from the 21st to 240th positions of SEQ ID NO: 70;

(5) a heavy chain comprising an amino acid sequence from the 18th to 461st positions of SEQ ID NO: 64, and a light chain comprising an amino acid sequence from the 21st to 240th positions of SEQ ID NO: 70;

(6) a heavy chain comprising an amino acid sequence from the 18th to 460th positions of SEQ ID NO: 66, and a light chain comprising an amino acid sequence from the 21st to 240th positions of SEQ ID NO: 70;

(7) a heavy chain comprising an amino acid sequence from the 18th to 462nd positions of SEQ ID NO: 62, and a light chain comprising SEQ ID NO: 108;

(8) a heavy chain comprising an amino acid sequence from the 18th to 461st positions of SEQ ID NO: 64, and a light chain comprising SEQ ID NO: 108; or (9) a heavy chain comprising an amino acid sequence from the 18th to 460th positions of SEQ ID NO: 66, and a light chain comprising SEQ ID NO: 108.

7. The method of claim 1, wherein the c-Met inhibitor comprises at least one selected from the group consisting of crizotinib, cabozantinib, foretinib, PHA-665752, SU11274, SGX-523, PF-04217903, EMD 1214063, golvatinib, INCB28060, MK-2461, tivantinib, NVP-BVU972, AMG458, BMS 794833, BMS 777607, MGCD-265, AMG-208, BMS-754807, JNJ-38877605, and pharmaceutically acceptable salts thereof.

8. The method of claim 1, wherein the IGF-1R inhibitor comprises at least one selected from the group consisting of an antibody, an aptamer, siRNA, shRNA, microRNA, a small-molecule IGF-1R inhibitor, and a pharmaceutically acceptable salt thereof.

9. The method of claim 1, wherein the IGF-1R inhibitor comprises at least one selected from the group consisting of linsitinib, NVP-AEW541, GSK1904529A, NVP-ADW742, BMS-536924, figitumumab, cixutumumab, dalotuzumab, R1507, XL-228, INSM-18, BMS-754807, AG-1024, GSK1838705A, PQ 401, and pharmaceutically acceptable salts thereof.

10. The method of claim 1, wherein the cancer is resistant to treatment with a c-Met inhibitor in the absence of an IGF-1R inhibitor.

11. The method of claim 10, wherein the cancer is resistant to treatment with an anti-c-Met antibody or antigen-binding fragment thereof in the absence of an IGF-1R inhibitor.

12. The method of claim 11, wherein the cancer is gastric cancer or lung cancer.

13. A pharmaceutical composition comprising a c-Met inhibitor and an IGF-1R inhibitor, wherein the c-Met inhibitor is an anti-c-Met antibody or an antigen-binding fragment thereof comprises:

a heavy chain variable region comprising a CDR-H1 comprising SEQ ID NO: 1, a CDR-H2 comprising SEQ ID NO: 2, and a CDR-H3 comprising SEQ ID NO: 3; and a light chain variable region comprising a CDR-L1 comprising SEQ ID NO: 10, a CDR-L2 comprising SEQ ID NO: 11, and a CDR-L3 comprising SEQ ID NO: 12, 13, 14, 15, or 16; or a heavy chain variable region comprising a CDR-H1 comprising SEQ ID NO: 1, a CDR-H2 comprising SEQ ID NO: 2, and a CDR-H3 comprising SEQ ID NO: 3, and a light chain variable region comprising a CDR-L1 comprising SEQ ID NO: 106, a CDR-L2 comprising SEQ ID NO: 11, and a CDR-L3 comprising SEQ ID NO: 13.

\* \* \* \* \*